(12) United States Patent (10) Patent No.: US 8,234,222 B2
Thompson et al. (45) Date of Patent: Jul. 31, 2012

(54) BENEFIT MANAGEMENT SYSTEM AND METHOD

(75) Inventors: John B Thompson, Bloomington, MN (US); Jeanne M Gilbert, Hudson, WI (US); Joel T Hernandez, Minneapolis, MN (US)

(73) Assignee: Benefit Resource, Inc., Bloomington, MN (US)

( * ) Notice: Subject to any disclaimer, the term of this patent is extended or adjusted under 35 U.S.C. 154(b) by 1997 days.

(21) Appl. No.: 10/327,518

(22) Filed: Dec. 20, 2002

(65) Prior Publication Data

US 2003/0229522 A1 Dec. 11, 2003

Related U.S. Application Data

(60) Provisional application No. 60/342,634, filed on Dec. 20, 2001.

(51) Int. Cl.
*G06Q 10/00* (2012.01)
(52) U.S. Cl. .................. 705/322; 705/2; 705/4; 705/35; 705/36 R; 705/37; 705/320
(58) Field of Classification Search ........................ 705/35
See application file for complete search history.

(56) References Cited

U.S. PATENT DOCUMENTS

| | | | |
|---|---|---|---|
| 5,794,207 A | 8/1998 | Walker et al. | |
| 6,078,890 A * | 6/2000 | Mangin et al. ..................... | 705/2 |
| 6,327,628 B1 | 12/2001 | Anuff et al. | |
| 6,356,910 B1 | 3/2002 | Zellweger | |
| 6,370,541 B1 | 4/2002 | Chou et al. | |
| 6,401,079 B1 | 6/2002 | Kahn et al. | |
| 6,463,461 B1 | 10/2002 | Hanson et al. | |
| 2001/0034622 A1 | 10/2001 | Davis | |
| 2001/0037223 A1* | 11/2001 | Beery et al. ........................ | 705/4 |
| 2002/0002475 A1 | 1/2002 | Freedman et al. | |
| 2002/0032639 A1* | 3/2002 | Hausken et al. ................ | 705/37 |
| 2002/0049617 A1 | 4/2002 | Lencki et al. | |
| 2002/0069090 A1* | 6/2002 | De Grosz et al. .................. | 705/4 |
| 2002/0095316 A1* | 7/2002 | Toan et al. ........................ | 705/4 |
| 2002/0124188 A1* | 9/2002 | Sherman et al. .............. | 713/201 |
| 2002/0149616 A1 | 10/2002 | Gross et al. | |
| 2002/0184045 A1* | 12/2002 | VanDeursen ....................... | 705/1 |
| 2003/0009355 A1* | 1/2003 | Gupta ............................... | 705/2 |
| 2003/0018498 A1* | 1/2003 | Banks ............................... | 705/4 |
| 2003/0023641 A1* | 1/2003 | Gorman et al. ................ | 707/530 |
| 2003/0050811 A1* | 3/2003 | Freeman et al. ................... | 705/7 |
| 2003/0074229 A1* | 4/2003 | Heise et al. ........................ | 705/4 |
| 2005/0055299 A1* | 3/2005 | Chambers et al. .............. | 705/36 |

OTHER PUBLICATIONS

Stetzler, Ames. "Kassebaum-Kennedy Law Creates More Hassles," Kansas City Business Journal, (Nov. 14, 1997).*

(Continued)

*Primary Examiner* — Elizabeth Rosen
(74) *Attorney, Agent, or Firm* — Mueting Raasch & Gebhardt, P.A.

(57) ABSTRACT

A benefit management system and method provides a portal-based information management and collaborative business process application. Preferably, the system and method is focused at the benefit broker/consultant and is configured to capture employee benefit management data, such as demographic data and plan data. Further, preferably, one or more users are provided with customized user access to the centralized application for use in performing one or more various benefit plan management functions, such as, for example, marketing, plan design; enrollment; administration; and communication between one or more application users.

31 Claims, 16 Drawing Sheets

OTHER PUBLICATIONS

BRI Home page accessed using Wayback Machine at http://web.archive.org/web/20010617183906/http://www.bri.com/ [retrieved from the Internet on Feb. 13, 2003] 16 pgs. total.

BenefitMall™ Home page accessed at http://www.benefitmall.com/BenefitMallWeb/home/home.html [retrieved from the Internet on Jul. 30, 2003] 10 pgs. total.

BenefitPoint™ Home Page accessed using Wayback Machine at http://web.archive.org/web/20011006194112/http://www.benefitpoint.com/index.html [retrieved from the Internet on Feb. 13, 2003] 3 pgs. total.

Benelogic™ Home Page accessed at http://www.benelogic.com/press/06-09-01.asp [retrieved from the Internet on Jul. 30, 2003] 1 pg. total.

ChannelPoint Home Page accessed using Wayback Machine at http://web.archive.org/web/20011217181017/http://www.channelpoint.com/ [retrieved from the Internet on Feb. 13, 2003] 1 pg. total.

eBenX Home Page accessed using Wayback Machine at http://web.archive.org/web/20011004165210/http://www.ebenx.cotn/index.html [retrieved from the Internet on Feb. 13, 2003] 3 pgs. total.

Employease Home Page accessed using Wayback Machine at http://web.archive.org/web/20001212232900/http://employease.com/index.html [retrieved from the Internet on Feb. 13, 2003] 4 pgs. total.

Sageo™ Home Page accessed at http://1b31.resources.hewitt.com/sg1dgp5/tbiappt200?nodeId=GreetingPage&clientId=08536 [retrieved from the Internet on Jul. 30, 2003] 2 pgs. total.

* cited by examiner

BENEFIT MANAGEMENT SYSTEM AND METHOD

CROSS-REFERENCE TO RELATED APPLICATIONS

This application claims the benefit of U.S. Provisional Application Ser. No. 60/342,634, entitled "BENEFIT MANAGEMENT SYSTEM AND METHOD," filed 20 Dec. 2001, wherein such document is incorporated herein by reference.

BACKGROUND OF THE INVENTION

The present invention relates generally to the management of employee benefits. More particularly, the present invention pertains to systems and methods for managing and/or controlling the delivery of employee benefits.

In the United States, an enormous number of individuals participate in an employment-based benefit program that, at a minimum, consists of health insurance. For example, health and welfare benefits may cost $4,000 to $5,000 per employee per year. In aggregate, employee benefits are a very large market, and even larger if retirement-related benefits are included. A large amount of economic resources is spent every year on benefit procurement and administration.

An employer (e.g., a benefit plan sponsor) that desires to start a new or change an existing benefit plan can either internalize or outsource the business process. Most companies do not have the internal resources required to deal with the myriad of benefit providers, products and the redundant, paper-driven processes necessary to gather, report and maintain the required benefit information. Thus, benefit broker/consultants (e.g., independent brokers or benefit broker/consultant firms) are used to facilitate the procurement of benefits for the vast majority of workers employed by small to mid-sized employers. As a result, benefit broker/consultants hold the key professional relationships with employers and benefit providers in the benefit supply chain. The remaining U.S. workers are typically employed by large companies who often, but not always, use their own internal resources to evaluate, select and administer their benefit programs.

The benefit broker/consultant market is a highly fragmented industry, with 90% of firms employing less than 10 people. Labor-intensive and paper-driven activities plague the industry, resulting in long sales cycles, high costs, increasing customer dissatisfaction and a lack of cost effective, comprehensive benefit program solutions. Paper processing, manual document development, repetitive phone calling, duplicative hard copy printing/faxing/mailing and vulnerability to human error characterize these inefficient administrative processes. It is estimated that 90% of all benefit transactions are handled by paper.

The benefit industry has not yet developed the technology to resolve these problems because the benefit industry, due to its complexity and fragmentation, has historically focused more on pricing and revenue gains, than on expense reduction and productivity. The benefit consumers (e.g., employers and employees) have borne the cost burden of the industry's supply chain inefficiencies.

The industry has been largely ignored by software developers due to its fragmented nature and complex business processes. Furthermore, benefit brokers do not have the resources (e.g., financial, time, people resources), nor the expertise to develop and maintain the technology themselves. Benefit providers, primarily insurance companies, are insular in nature and are focused on internal processes and communications. This has resulted in isolated legacy systems, a lack of common standards, and far less business automation than other service providers, such as banks and investment firms.

Although the high distribution costs and inefficiencies of the benefit supply chain have historically been borne by the buyers (e.g., employers and employees), powerful new trends are emerging that will shift the paradigm to the advantage of the benefit consumer. For example, major regulatory change is occurring. Government action is triggering profound structural changes in the industry by forcing the transition from paper-based to electronic communications. The Health Insurance Portability and Accountability Act of 1996 ("HIPAA") establishes electronic transaction standards and code sets, along with privacy and security standards for the health care industry. Further, health care costs and high levels of employer and employee dissatisfaction are increasing. The benefit industry is under increased pressure to reform itself.

Within the benefit supply chain, benefit providers (e.g., insurance companies) underwrite the products that intermediaries (e.g., benefit brokers) distribute to employers (e.g., plan sponsors) who enroll their employees for plan coverage. The benefit broker/consultant facilitates procurement of the vast majority of these plans as well as the accompanying administrative services that often are outsourced to third party vendors. Strategically positioned as the benefit distributor, the benefit broker/consultant may represent up to hundreds of employer/clients and many benefit providers. Although large corporations often deal directly with benefit providers, benefit distribution is largely controlled by benefit broker/consultants.

Although various products are currently being used in the benefits supply chain, they do not effectively address the problems as discussed above. For example, many companies (e.g., an intermediary company) offer specific, limited products and/or services that require customers to use their intermediary company proprietary portal, thereby inserting an additional cost, image and distribution component into the benefit supply chain. Others provide little more than electronic enrollment systems. Additionally, most companies have not provided an adequate reduction in paperwork. Their systems typically do not directly connect to the benefit broker, the benefit provider and employer. In other words, a direct result of such a process is that data often has to be re-keyed, particularly in a plan set-up stage.

These companies provide varying combinations of the pre-sale and post-sale processes that make-up the employee benefits business cycle. For example, such processes include pre-sale services like enterprise management or benefit plan marketing and procurement; or post-sale services like benefit provider plan installation, plan enrollment, plan administration, or plan premium remittance.

SUMMARY OF THE INVENTION

The present invention provides an efficient and low cost benefit delivery and management system and method. Preferably, it is a portal-based information management and collaborative business process application that empowers the benefit industry to electronically design, market, purchase and/or administer benefits, thereby replacing the paper-driven processes that currently plague the benefit supply chain. This transformation will drive large-scale productivity gains resulting in administrative expense reductions, lower product pricing, reduced human error, and/or vastly improve customer choice and satisfaction.

The present invention is preferably aimed at the fulcrum of the benefit supply chain, i.e., the benefit broker/consultant. It reengineers the benefit broker/consultant's business processes with a dynamic, integrated, interactive and personalized application that will manage their customer and benefit provider relationships on a mass scale. The present invention captures the essential employer and employee benefit information in a seamless, transparent, integrated, automated and customizable format, giving the user total access to and control of various key benefit plan management functions, such as: marketing, enrollment, administration and communication.

Advantageous use of the present invention by benefit broker/consultants is not dependent on, nor does it require, participation by benefit providers. However, benefit provider participation may enhance operational efficiencies. The present invention can be used to shift daily plan administrative responsibility from the benefit provider to other benefit supply chain participants. Benefit providers may no longer be required to manually load, enter, or maintain benefit plan data. The present invention is preferably able to automate the time-consuming, labor intensive, paper-driven plan processes such as request for proposals (RFP) responses, installation and enrollment, eligibility verification, premium remittance, commission accounting and licensing. The substantial cost savings associated with these administrative reductions provide incentive for benefit providers to participate. Furthermore, the present invention may give benefit providers real-time access to market and demographic business information through intelligent capturing of customer transactional data from their sales channel (e.g., the benefit broker/consultant).

Additionally, because the present invention can reassign many of the daily business processes to the lowest common user in the benefit supply chain, providers may be freed to focus resources on product development, risk management, customer relationship building, claims management and employee education and training.

Preferably, revenue to the application administrator of the functionality of the present invention is received through fees, e.g., subscription-based fees, paid by the benefit broker/consultant. For example, the benefit broker/consultant charges its employer/clients a negotiated fee for their collaborative access and use to one or more functional portions of the application. Preferably, although this may occur, the administrator does not charge a fee to sellers of benefits (e.g., benefit providers) or buyers of benefits (e.g., employers/employees).

The present invention delivers an immediate value to the benefit broker/consultant. Preferably, it automates and streamlines day-to-day business processes resulting in, preferably, a paperless working environment. As a business enterprise platform, the present invention preferably performs both as an intranet and an extranet. For example, it may not just provide an application portal that a benefit broker/consultant will visit occasionally to expedite their sales cycle, but rather may preferably provide their own image-branded portal that provides a total, end-to-end services solution, or at least a portion thereof. It empowers the benefit broker/consultant with image branding, customization, and portal personalization tools to use internally and to private label with their employer/clients and benefit providers.

The present invention, at least in one embodiment, delivers a full range of pre-sale and post-sale services that comprise the benefit business cycle. For example, this is demonstrated in the detail and intelligence of the customizable benefit plan design functionality which is a central enabling process used to automate benefit plan management functions such as marketing, administration and communication.

The present invention provides one or more various functions. For example, along with various other functionality as shall be described in detail herein, employee self service (ESS) benefit functionality is included. Further, for example, benefit broker/consultants may own their own data. In addition, the present invention provides robust data reporting and knowledge sharing functionality, and further is designed to be HIPAA compliant.

A method for use in providing employee benefit management services according to the present invention includes providing an application operable to perform one or more employee benefit functions using an associated relational database configured to store employee benefits management plan data. The employee benefits management plan data includes at least one benefit plan derived from at least one benefit plan design creation template. The at least one benefit plan design creation template comprises at least a plurality of selectable benefit plan details quotable by more than one benefit provider of a plurality of benefit providers. Further, the application includes a plurality of presentation panels for use in providing information to a user. The presentation panels are configured to provide at least one of user perceivable graphical elements and user interaction graphical elements; the at least one benefit plan design creation template is configured as at least one presentation panel. At least one application portal is provided to allow at least one authorized user access to the application. The at least one application portal is extendable to one or more additional authorized users by the at least one authorized user to permit the one or more additional authorized users access to all or a limited portion of at least one of the presentation panels and the employee benefits management plan data. The application is accessed by an authorized user such that the authorized user through a plan creator user interface provided by the at least one presentation panel can create a benefit plan using the benefit plan design creation template. The plurality of the selectable benefit plan details of the benefit plan design creation template are provided to the authorized user in a dynamic, multi-level format such that selection by the authorized user of one or more of a plurality of options associated with at least one selectable benefit plan detail displayed to the authorized user determines a plurality of selectable benefit plan details and one or more associated benefit plan options (e.g., valid options) to be subsequently displayed to the authorized user.

Another method for use in providing employee benefit management services according to the present invention includes providing an application operable to perform one or more employee benefit functions using an associated relational database configured to store employee benefits management plan data and allowing one or more users access to the application via one or more user portals. The one or more users include at least one of a benefit/broker consultant, an employer/client, an employee, and a benefit provider, and further, allowing one or more users access to the application includes providing customized access through the one or more user portals such that at least one user has different access rights relative to another user. Further, the method includes opening at least one user portal such that at least one of the one or more users through a plan creation user interface can create a benefit plan using the employee benefits management plan data.

In another method for use in providing employee benefit management services according to the present invention, the method includes providing a central application operable to perform one or more employee benefit functions using an associated relational database configured to store employee benefits management plan data and providing a benefit provider via a user portal with access to all or certain portions of the employee benefits management plan data. A benefit/broker consultant, via a user portal, is provided access to all or certain portions of employee benefits management data and the benefit/broker consultant is allowed to provide one or more employer/clients access to all or certain portions of the employee benefits management data.

Yet another method for use in providing employee benefit management services is described according to the present invention. The method includes providing an application operable to perform one or more employee benefit functions using an associated relational database configured to store employee benefits management plan data. The application includes a plurality of presentation panels for use in providing information to a user; the presentation panels are configured to provide at least one of user perceivable graphical elements and user interaction graphical elements. The application is accessible via one or more user portals customizable to permit one or more users access to all or a limited portion of at least one of the presentation panels and/or employee benefits management plan data. Further, personalized image branding of one or more presentation panels used to provide one or more user interfaces with the one or more users is provided. The personalized image branding includes selection of one or more characteristics of one or more of the user interfaces displayed to the one or more users.

Yet another method for use in providing employee benefit management services according to the present invention includes providing an application operable to perform one or more employee benefit functions using an associated relational database configured to store employee benefits management plan data. The application includes a plurality of presentation panels for use in providing information to a user; the presentation panels are configured to provide at least one of user perceivable graphical elements and user interaction graphical elements. The method further includes providing a benefit broker/consultant portal to allow at least one benefit broker/consultant access to the application and providing at least one extension of the benefit broker/consultant portal as at least one satellite portal. The at least one satellite portal is separately configurable by the benefit broker/consultant to extend certain rights to one or more employer/clients for access to the application. Security authorization to control access of at least one of the benefit broker/consultant and the employer/clients to one or more portions of at least one of the presentation panels and/or employee benefits management plan data is provided. In one embodiment of the method implementing satellite portals, one or more child portals corresponding to the one or more employer/clients may also be provided; wherein each child portal is an extension of the access extended to the respective one or more employer/clients and permits each of the one or more employer/clients to further extend access to the application to one or more additional users. The one or more additional users include at least one employee of at least one of the one more employer/clients.

One or more methods according to the present invention may include one or more of the following features: allowing an authorized user to access the application to input demographic plan data, wherein the demographic plan data includes at least one of employer/client and employee/dependent data; generating a benefit plan request for proposal including at least one benefit plan in conjunction with demographic plan data; generating a benefit plan request for proposal calculated response based on a benefit plan request for proposal; generating, at an external benefit provider, a benefit provider request for proposal response based on a benefit plan request for proposal; allowing one or more of a benefit/broker consultant, an employer/client, an employee, and a benefit provider to access all or a limited portion of at least one of presentation panels and employee benefits management plan data (e.g., access to create, delete or modify a benefit plan and/or to create, delete or modify demographic plan data); allowing an employer/client to perform one or more employee benefit management functions (e.g., access to change demographic data associated with the benefit plan); allowing an employee, after an employer/client has adopted a benefit plan, access to at least a portion of the employee benefits management data (e.g., benefit provider plan information); maintaining the benefit plan based on changes in associated employee/dependent demographic plan data and/or providing plan change notification relating to the modification of the benefit plan; mining the employee benefits management plan data for use in generating at least one of a plurality of reports; personalized image branding one or more presentation panels used to interface with one or more of a benefit broker consultant, an employer/client, an employee, and a benefit plan provider; accessing at least one portal using at least an interact connection; providing at least one extension of the benefit broker/consultant portal as at least one satellite portal, wherein the at least one satellite portal is separately configurable by the benefit broker/consultant to extend certain rights to one or more employer/clients for access to the application portal; providing one or more child portals corresponding to the one or more employer/clients, wherein each child portal is an extension of the access extended to the respective one or more employer/clients and permits each of the one or more employer/clients to further extend access to the application to one or more additional users, wherein the one or more additional users comprise at least one employee of at least one of the one more employer/clients; and providing security authorization to control access of users to at least one of portions of the presentation panels and/or employee benefits management plan data (e.g., providing view controllable security of the one or more presentation panels such that access to view or edit the presentation panels is restricted and/or providing data security such that user access to view or edit data of one or more presentation panels is restricted).

A system according to the present invention may include one or more of the following features, or other features for use in implementing functionality described herein: a central application operable to perform one or more employee benefit functions using an associated relational database configured to store employee benefits management plan data; an application accessible via one or more user portals by a benefit provider and a benefit/broker consultant; a central application that allows the benefit/broker consultant via a user interface to provide one or more employer/clients access to all or certain portions of the employee benefits management data; an application that allows a employer/client, via an interface, to provide one or more employees thereof with access to all or certain portions of the employee benefits management data; an application that allows the benefit/broker consultant or the employer/client to be a plan creator, wherein the plan creator is allowed through a plan creator user interface to create a benefit plan using the employee benefits management plan data; an application that allows one or more of a benefit/broker consultant, an employer/client, an employee, and a benefit provider to create, delete or modify one or more portions of a benefit plan via a user interface and/or that allows one or more of a benefit/broker consultant, an employer/client, an employee, and a benefit provider to create, delete or modify one or more portions of demographic plan data via a user interface; a central application that provides a graphical user interface to allow for input of demographic plan data, wherein the demographic plan data comprises at least one of employer/client and employee/dependent data; an application that is operable to generate a benefit plan request for proposal comprising at least one benefit plan in conjunction with the demographic plan data; a central application that is further operable to generate a plan request for proposal calculation response; a central application that allows access to the benefit plan request for proposal by a benefit provider and provides the benefit provider a user interface for use in providing a request for proposal response; a central application that permits the benefit broker consultant or an employer/client to perform personalized image branding of one or more user interfaces; an interface so as to provide access to one or more of the user portals using an internet connection; a plurality of presentation panels for use in providing information to a user, wherein the presentation panels are configured to provide at least one of user perceivable graphical elements and user interaction graphical elements; a central application that provides security authorization to control access of at least one of the benefit/broker consultant, an employer/client, and a benefit provider to at least portions of the presentation panels and/or the employee benefits management plan data; a central application that provides support for at least one extension of the benefit broker/consultant portal as at least one satellite portal, wherein the at least one satellite portal is separately configurable by the benefit broker/consultant to extend certain rights to one or more employer/clients for access to the application; and a central application that supports the provision of one or more child portals corresponding to the one or more employer/clients, wherein each child portal is an extension of the access extended to the respective one or more employer/clients and permits each of the one or more employer/clients to further extend access to the application to one or more additional users, wherein the one or more additional users comprise at least one employee of at least one of the one more employer/clients.

DETAILED DESCRIPTION OF THE EMBODIMENTS

Figure 1A:
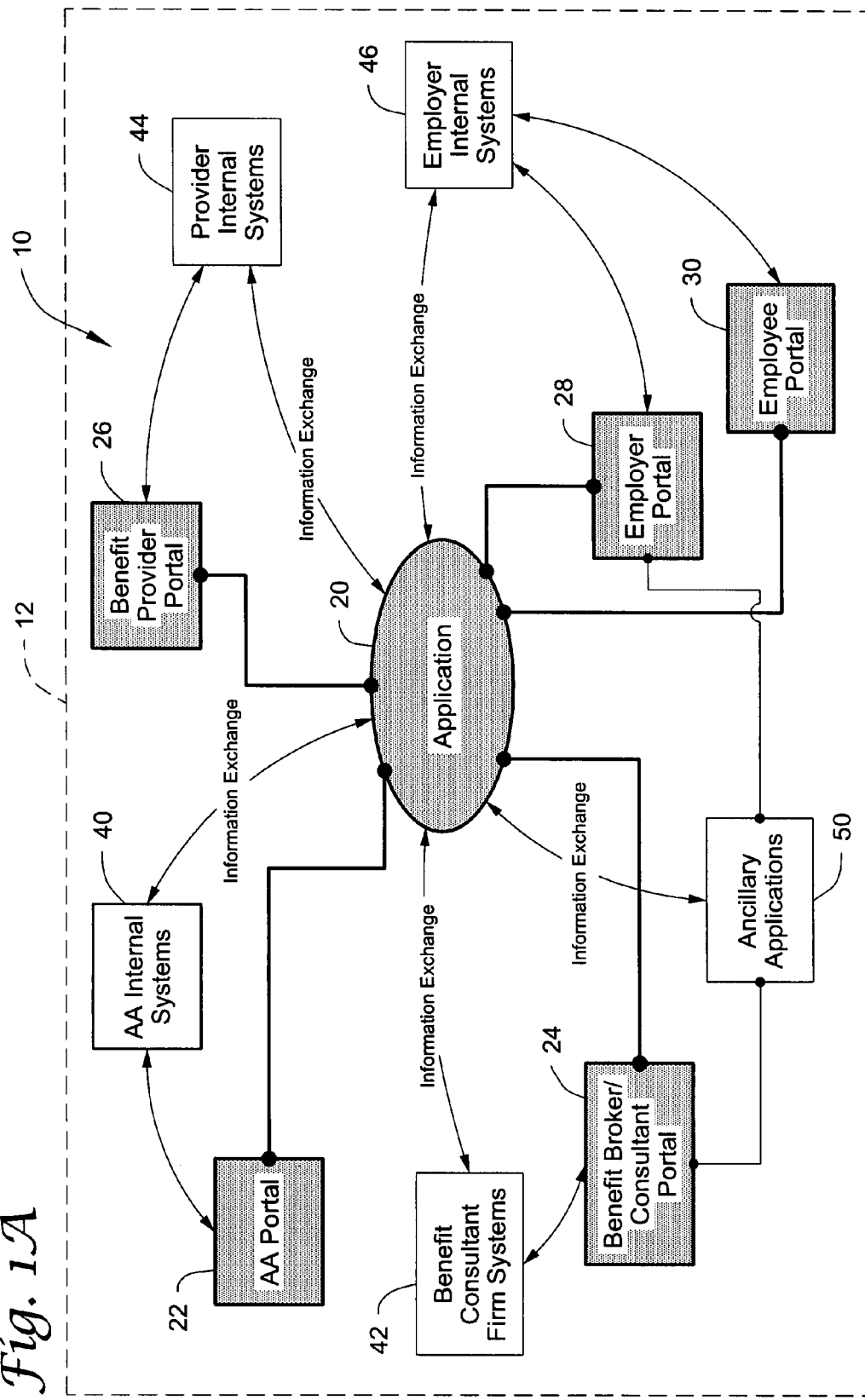
FIG. 1A is a general diagram showing the general functionality of a system and/or method according to the present invention for benefit management.
Figure 1B:
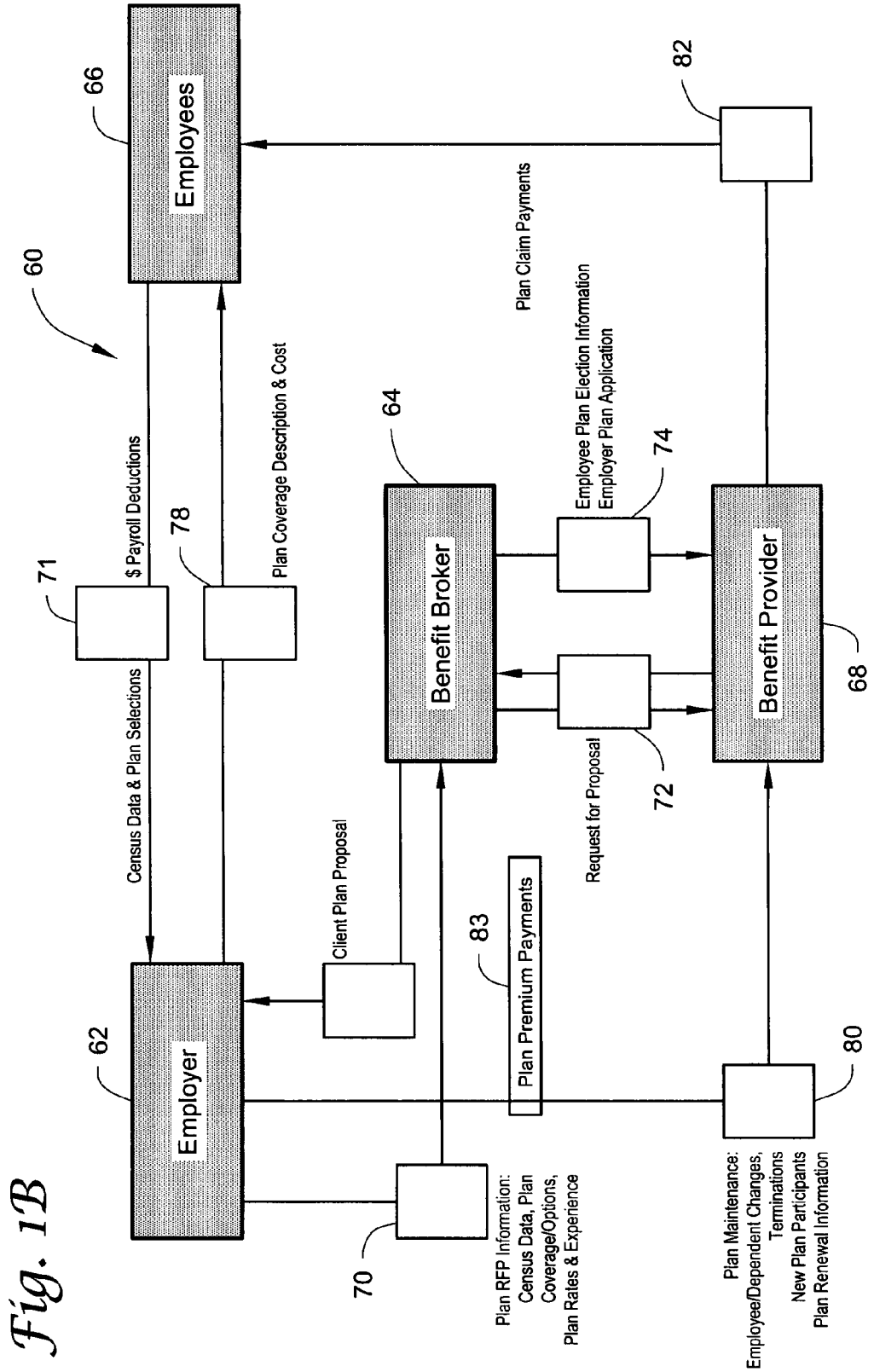
FIG. 1B is a block diagram showing the workings of a benefit supply chain.

The present invention shall be described generally with reference to FIGS. 1A-1B. Thereafter, one or more embodiments of the present invention shall be described with reference to the remaining figures.

FIG. 1A shows a diagram that illustrates a multi-view portal functionality and workflow method 10 that can be implemented via a hardware and software architecture 12 according to the present invention. The method 10 addresses the needs of the benefit supply chain 60 shown generally in FIG. 1B. Generally, a benefit broker/consultant 64 facilitates procurement by employer/clients 62 of benefit plans including products from one or more benefit providers 68. The employer/clients 62 procure such benefits under the benefit plans on behalf of their employees 66.

For example, generally the benefit broker/consultant 64 collects benefit plan information 70 used for a request for proposal (RFP). Such plan RFP information 70 may include, for example, census data, plan coverage/options, plan rates, and plan experience information. With such information, the benefit broker/consultant 64 provides an RFP 72 to one or more benefit providers 68 in anticipation of an RFP response therefrom. Upon return of the responses, the benefit broker/consultant 64 may then put together a client plan proposal 76 for the employer/client 62 providing information to the employer/client 62 allowing the employer/client 62 to make a decision as to the benefit plan to select.

Upon selection of a benefit plan, enrollment and installation of the benefit plan must be provided. For example, census data and plan selections by employees 66 may be provided to the employer/client 62 along with payroll deduction information (block 71). The employer/client 62 generally provides such information to a benefit broker/consultant 64 so that such employee plan election information and an employer plan application 74 can be provided to the benefit provider 68. Upon installation of the plan, plan coverage description and cost is provided to the employees 66, e.g., a summary plan description.

After installation of the plan, plan maintenance 80 must be provided by the benefit supply chain 60. For example, such plan maintenance 80 may include employee/dependent changes, terminations of employees, adding of new plan participants, plan renewal information for renewing the benefit plan, etc.

Also, plan premium payments 83 by the employer/client 62 to the benefit provider 68, as well as plan claim payments 82 from the benefit provider 68 to the employee 66, are facilitated by one or more parties in the benefit supply chain 60.

The portal functionality and workflow method 10 includes an integrated, collaborative business process application 20 that provides a customizable portal infrastructure for a plurality of different users, preferably for carrying out one or more, and preferably many, of the functions provided in the benefit supply chain 60. For example, in one embodiment, and as shown in FIG. 1A, preferably the portal infrastructure includes one or more of an application administrator portal 22, a benefit broker/consultant portal 24, an employer/client portal 28, an employee portal 30, and a benefit provider portal 26. The application 20, preferably, at least in one embodiment, performs as the centralized hub of the benefit supply chain 60 by providing a universal technological platform for a plurality of users, such as, for example, the benefit broker, employer, employee, and benefit provider.

Although any number of different types of application users may benefit from the present invention, preferably the application users represent all the key benefit supply chain components. For example, the users may be a benefit/broker consultant which, generally as used herein, is preferably representative of a benefit broker/consultant and/or a benefit/broker consultant firm (including employees thereof) that may have access to perform one or more of the functions as described in a table provided herein. Preferably a benefit broker/consultant is a state licensed group insurance broker and/or firm selling employee benefit products and services to employers/clients (such a definition of a benefit broker/consultant includes independent brokers).

An application user may also be an employer/client. As generally used herein, an employer/client is preferably any legal entity that sponsors the benefit product and/or service on behalf of their employees. Although the employer/client may be a direct customer/client of the application administrator as opposed to being an employer/client of a benefit broker/consultant, preferably, according to the present invention, the employer/client is a customer or client of the benefit broker/consultant. As a client of the benefit broker/consultant, the employer/client may be authorized by the benefit broker/consultant to access and perform one or more functions such as those described in the table provided herein.

Further, an application user may be an employee that is individually eligible for benefit coverage because of his or her association with the employer/client. Dependent information is part of the employee record. An employee may have functionality access to the application for functional purposes as authorized by the employer/client. For example, employees may be allowed to view and/or perform authorized benefit program management functions such as described in the table herein.

Yet further, a benefit provider may also be an application user. A benefit provider is generally and preferably described herein as a supplier of the employee benefit products and/or services. A benefit provider may have access to the functionality as described in the table herein.

The application administrator (e.g., the maintainer of the centralized application 20, and preferably, the seller of services such as access to the application 20 to a benefit broker/consultant and/or an employer/client) will also have one or more functions and access to the application as described in the table herein.

The application 20 manipulates, uses, processes, adapts or otherwise handles various types of employee benefits management plan data. As used herein, employee benefits management plan data may include any data that is so handled or even not handled by the application 20, including data that directly or even indirectly relates to employee benefits. For example, such data includes, but is clearly not limited to, specified employer, employee/demographic data; inforce, historical, and/or proposed benefit plan (e.g., life, long term disability, medical, etc.) details in digitized format; summary plan descriptions; employee handbooks; employee benefit statements; premium remittance data; commission accounting data; benefit communications data such as plan specific notifications; and a wide range of report data.

As shown in FIG. 1A, various systems, such as internal systems associated with the various users, are used in providing information exchange between the users who are given access to the application 20 and the centralized application 20. For example, application administrator internal systems 40 may be used in providing information exchange between the application 20 and application administrator portal 22, benefit consultant firm systems 42 may be used in providing information exchange between application 20 and the benefit broker/consultant portal 24, benefit provider internal systems 44 may be used in providing information exchange between application 20 and the benefit provider portal 26, and employer/client internal systems 46 may be used in the exchange of information between the application 20 and the employer/client portal 28, and also between the application 20 and the employee portal 30.

Yet further, ancillary applications, such as, for example, accounting functionality, payroll functionality, etc., may also be used in the provision of information exchange being facilitated between the application 20 and the benefit broker/consultant portal 24 and/or the employer/client portal 28.

The application 20 provides for certain functionality or, in other words, content and business automation. For example, at least in one embodiment, the application 20 provides a business center, a client management center, a plan designer, plan marketing/benefit exchange functionality, experience-rated external market search and request for proposal (RFP) functionality, benefit provider RFP response tracking functionality, client plan proposal presentation, plan administration, as well as risk management.

For example, the business center may provide the benefit broker/consultant with one or more of the following business type functions:

Company Calendar—Both personal and shared views for meeting and appointment scheduling.

Time Management—Time tracking tools that map to a calendar and client folders.

Expense Management—Expense tracking tools that map to a client folder.

Contact Management—Electronic rolodex to manage vendor, provider and personal contacts.

Licensing—Insurance license, provider appointment and continuing education tracking tool.

Commission Accounting—Electronic reconciliation of premium to commission.

Sales Force Automation—Prospect and client management reporting.

Executive Reporting—Firm level general ledger, client expense and other advantageous reports.

Benefit Broker/Consultant Firm Management Center—Business center to create and manage proprietary marketing materials and formats.

Benefit Provider Library—A shared module to access benefit provider specific information including ratings, products, services, company forms and commission schedules.

E-reference Library—A shared module that contains hyperlinks to industry recognized life and family informational resources.

For example, the client management center may provide the benefit broker/consultant with one or more of the following functions that relate to the relationship with one or more employer/clients:

Client Contact Management—Electronic client rolodex.

Employee Self-Service—Employee access to view and edit their personal benefit information.

Employer/Employee Demographics—Employer personnel, business and risk profile information manageable on a location by location basis.

HIPAA Compliance—Electronic enforcement of privacy, security and user authentication standards required by HIPAA.

Satellite Site—Employer portal access to their business and employee benefit information.

Employee Health Care Manager—A planner that allows a user to manage and track personal and family healthcare information.

The customizable benefit plan designer, e.g., a designer that uses templates to assist in building plans, is at least one central enabling process to perform benefit plan functions, such as, for example, marketing, administration and communication. For example, the application's product plan design templates usable to build benefit plans may include, for example, Life, AD&D, Medical, Dental, Disability, Long-Term Care, Vision, Legal, Prescription Drug, Critical Illness, Business Travel Accident, and 401(k).

The customizable plan templates are documented in contract level detail referred to as valid options with the values provided for user selection via a user interface provided by the architecture 12 used to implement the functionality. The templates are intelligent because a user option value will drive the subsequent series of options for selection in building the plan. Options that are ruled-out based on user selection are not displayed, ensuring that only valid plan data is gathered. The templates allow users to create unique values by populating a "notes" category. This feature ensures design flexibility for total plan customization and captures the information necessary to evolve the application.

In other words, the application provides or is otherwise operable to create benefit plans using a benefit plan design creation template. Generally, a benefit plan design creation template includes at least a plurality of selectable benefit plan details quotable by more than one benefit provider of a plurality of benefit providers. The application 20 (e.g., via a plurality of presentation panels for use in providing information to a user and which are configured to provide at least one of user perceivable graphical elements and user interaction graphical elements) provides the benefit plan design creation template as at least one presentation panel.

An authorized user is allowed access to the application 20 such that the authorized user through a plan creator user interface provided by the at least one presentation panel can create a benefit plan using the benefit plan design creation template. The plurality of the selectable benefit plan details of the benefit plan design creation template are provided to the authorized user in a dynamic, multi-level format such that selection by the authorized user of one or more of a plurality of options associated with at least one selectable benefit plan detail displayed to the authorized user determines a plurality of selectable benefit plan details and one or more associated benefit plan options to be subsequently displayed to the authorized user. Through interaction with the creation template by the user interface, the user can build a plan for use in a benefit plan request for proposal. Such built plans may be created for use by a single client or may be built for use as a standard plan design for use with multiple clients.

The application 20 automates benefit marketing for a user, such as the benefit broker/consultant, with a single entry, multiple carrier interface (SEMCI). Plan marketing functionality may, for example, provide one or more functions such as the following:

Experience-Rated External Market Search and Request for Proposal (RFP) Tools and System-Populated Templates for performing same.

Provider RFP Response Tracking.

Client Proposal Presentation Analysis Tools and System-Populated Templates.

The experience-rated external market search and request for proposal (RFP) functionality is designed for employer/clients that require an experience-rated, individually underwritten plan for any of the following reasons:

Customized benefit plan design is desired.

Employer demographics.

Employer/dependent demographics

Industry

Plan financial experience

The application 20 may be used to custom-generate each benefit plan RFP that can be sent to one or more benefit providers in anticipation of a response therefrom. Application business intelligence guides the business process to ensure that only required plan information is included. Preferably, the user determines which benefit provider(s) receive an RFP. Further, preferably, the portal view has a built-in RFP response format that does not require electronic data transfer with the benefit provider.

The application 20 can be used to track, monitor and record benefit provider responses and includes a view function that allows the user to review each proposal to determine whether to include it in a client proposal guided by the benefit broker/consultant and provided to a employer/client thereof. A collaborative note window may also be attached to each RFP to document and archive all underwriting communications between the benefit broker, employer, benefit provider salesperson and/or underwriter.

Further, the application 20 offers unique, automated and customizable client proposal functionality with presentation tools. As will be described further herein, in one embodiment, for example, benefit plan proposals can be displayed in an employer/client satellite site within the benefit broker/consultant's portal.

Yet further, one or more of the following plan administration services may be automated with embedded analytics to perform at a user's desktop:

Eligibility Administration—A system-automated tool to determine employee plan eligibility. The employee record may be electronic from employment date to termination date.

Remittance Reconciliation—A system-generated monthly report that reconciles plan enrollment data with plan rates to calculate the premium amount due.

Notifications—System-generated employment and benefit change notices.

Enrollment—Employee plan enrollment.

Renewal—The process of extending the inforce plan beyond the plan anniversary to a new plan year.

Amendment—The process of changing the inforce plan detail to reflect new plan revisions.

Commission Tracking—Reconciliation of plan premium to provider commission schedule.

HIPAA Compliance—Meeting regulatory standards for privacy, security, logging and auditing.

Successful risk management require that all essential employer and employee information be captured and maintained in a single source (e.g., database/data warehouse) as is provided by the present invention. Risk management includes mitigating company risk through ongoing communication of company policies and practices to employees, providing prospective benefit providers with accurate plan information for risk evaluation, acceptance and pricing leverage and meeting government regulatory requirements, as are also preferably provided by the present invention. The centralized application 20 is the ideal risk management tool to minimize risk for users, such as, for example, the employer, benefit provider and benefit broker.

Further, application 20 includes one or more of the following types of functionality:

Access functionality: The benefit broker/consultant can record, view and process essential firm, client and benefit provider information 24 hours a day, 7 days a week (in other words, 24/7); for example, by using a browser-enabled search engine.

Collaborative functionality: Clients and benefit providers may be provided customized portal access and functionality to manage and share information.

Data Implementation/Migration Tools: Predefined formats may be used for importing client information.

Data Management functionality: Parametized reporting, logging and auditing can be performed.

Data Security functionality: Role and/or task based user access and authentication can be implemented.

Ease of Use functionality: Users may have point and click ability; for example, access to the system from any browser-enabled desktop and/or laptop.

Image Customization functionality: Benefit broker/consultants may "brand" their screen image with their firm identity (logo's, etc.) and "private label" their employer client image as described further herein.

Instant Messaging functionality: Rapid and secure communication is generally required and will be embedded within the application 20.

Internationalization functionality: The application 20 may contains tools to display information in multiple languages.

Peer-to-Peer File Sharing functionality: This may allow data to be stored at a client site and accessed through the application 20 via the instant messaging client.

Scanned Documents and Images functionality: May require data to be saved in a commonly-viewable format such as .gif, .jpeg, .pdf.

Personalization functionality: Individualized portal view, functionality and image.

Wireless functionality: The application 20 may contain a full-featured wireless mark-up language object library that can support wireless services.

As described above, the application 20 may contain image branding portal customization and personalization tools and templates. For example, each benefit broker/consultant can display their own name, logo and colors on user interface screens. This allows benefit broker/consultants to "private label" the image display feature of the application 20 for their employer/clients. This reinforces their value-added role as a benefit and technology consultant to the employer/client. Further, in their own portal, employer/clients can display the name and logo that employees will view while performing employee self service (ESS) benefit management tasks. For example, in one embodiment, users may select from 3 site structure templates, 3 graphic sets, 8 color pallets and 5 fonts; a total of 360 options to create their own unique look and feel. However, any number of branding features may be used.

To assist users in populating the application 20 with benefit management data, such as, for example, business and client information, the application 20 preferably provides pre-defined formats for importing data, e.g., client contacts, employee census and payroll information.

Data security functionality is provided to manage network design, implementation, and capacity monitoring; operating system and application server security and upgrade monitoring/implementation; back-up performance, capacity and management; as well as overall infrastructure design, security and performance management. Further, for example, transmission protection can be accomplished through the use one or more various transmission protection techniques, such as, encryption (e.g., for users of Netscape Navigator and Microsoft Internet Explorer).

User authentication through the use of ID's and passwords is preferably used to ensure access is restricted to the parameters of their assigned role. All system accesses will create an audit trail. Further, for security, the application 20 may provide that each client has their own specific database, e.g., a portion of a partitioned database.

Fast and efficient communications is also preferably provided for application users. For example, embedded instant messaging (IM) functionality may be used. This may provide a uniform communications environment for the benefit supply chain to instantaneously collaborate, resulting in improved efficiencies and reduced expenses. Instant messaging may also have a significant security role in reducing user reliance on commercial e-mail messaging, which can contain embedded viruses, resulting in work disruption and increased expenses. For example, the IM feature may include data encryption, along with an integrated archiving and threaded capability, to satisfy HIPAA security and audit requirements.

The application 20 is preferably user customizable (e.g., user portal views can be created and allowed to be accessed by authorization of one or more other users) by all the components of the benefit supply chain. For example, the application 20 may in one embodiment empower the benefit broker/consultant to assign user roles and task definitions (i.e., role-based access control) on a client-by-client basis to fit their unique needs. Further, the authorization may be extended to allow employee self service functionality to input, update, track and view various types of data and perform certain functionality, such as, for example, personal and dependent information as well as plan selection and enrollment.

The following table shows an exemplary embodiment of user roles and tasks that can be assigned.

| USER ROLE AND TASK CUSTOMIZATION MODEL | | | | |
|---|---|---|---|---|
| | Benefit Broker | Employer | Employee/ Dependent | Benefit Provider |
| Customized Image Branded Personal Portal Business Center | X | X | X | X |
| Company Calendar | X | X | X | |
| Time Management | X | X | X | |
| Expense Management | X | X | X | |
| Licensing | X | | | |
| Commission Accounting | X | | | |
| Sales Force Automation | X | | | |
| Executive Financial Reporting | X | | | |

-continued

USER ROLE AND TASK CUSTOMIZATION MODEL

| | Benefit Broker | Employer | Employee/ Dependent | Benefit Provider |
|---|---|---|---|---|
| HIPAA Compliance | X | X | | X |
| Resource Center | X | | | |
| Provider Library | X | X | X | X |
| Plan Demographics | X | X | X | X |
| Plan Design | X | X | X | X |
| Plan Marketing | | | | |
| Request for Proposal (RFP) | X | X | | X |
| Client Proposal | X | X | | X |
| Plan Administration | | | | |
| Amendments | X | X | | X |
| Communication | X | X | X | X |
| Desktop Customer Service | X | X | X | X |
| Enrollment | X | X | X | X |
| Maintenance | X | X | X | X |
| Premium Reconciliation | X | X | | X |
| Renewal | X | X | | X |
| E-Reference Resource Library | X | X | X | X |
| Data Maintenance | X | X | X | X |
| Data Mining and Reporting | X | X | X | X |
| Data Security | X | X | X | X |

The following scenarios illustrate the power of the application's multi-level user customization functionality. For example, upon implementation of the application, a benefit broker/consultant firm may specify security clearances and assignment of roles and tasks for its employees. Firm employees will perform specific tasks such as internal sales commission accounting, internal sales management as well as plan design, plan marketing and plan administration for their employer/clients.

Further, for example, for one of its employer/clients, the client and benefit broker consultant may mutually determine that the benefit broker firm will have total control and perform all the system functions on behalf of the employer.

Yet further, for example, for a different employer/client, the benefit broker firm and the client may determine that the employer wants to limit its direct use of the application 20 to that of a personalized employer portal. The firm thus grants the employer's human resource administrator access to view the current and archived plan information and perform limited plan maintenance functions (employee changes, terminations, new enrollees, etc.). The benefit broker firm retains the authority for plan design, plan marketing and many remaining plan administration functions.

In addition, for example, for a third employer/client, the human resource representative may be authorized to function as the plan administrator and collaborate with the benefit broker firm to perform key functions including benefit plan design, plan marketing and plan administration. A second human resource employee may be given restricted access to perform limited plan maintenance support tasks, as determined by the employer. In this scenario, an employer executive is allowed unrestricted access to view all plan information.

In another illustration, for yet another employer/client, the employer/client may elect to have a personalized employer portal and to provide personalized portals to its employees. The employer's designated plan administrator controls the plan design, plan administration and data mining/reporting functions. The company's employees may be granted access to individual personalized portals where they can view and perform restricted plan maintenance and plan enrollment tasks in addition to their personal healthcare planner and health statement archive. In this case, the benefit broker firm may only retain responsibility for the plan marketing function (e.g., external RFP process or internal marketing, such as with use of a rate calculation engine).

Yet further, in another scenario, the benefit broker firm may establish its own pricing/fee structure with each of its employer/clients.

The customizable user role and task functionality also extends to the benefit providers. Benefit providers preferably have controlled access to plan design, plan marketing and plan administration information and functionality through one or more shared portal views. For example, through a portal view, benefit providers may access one or more of the following business process platforms: Marketing, Sales, Underwriting, Communications, Enrollment, Desktop Customer Service, Premium Reconciliation and Remittance, Commission Accounting, Plan Amendments, and Plan Renewals.

Via the application 20, benefit broker/consultants may empower their employer/clients to self-manage many of their benefit information management tasks, including employee self service (ESS). The benefit broker/consultant may collaborate with their employer/clients to share task performance responsibilities and determine user roles and authority. The benefit broker/consultant can charge employers a technology access fee to empower employers (and/or employees) to efficiently self-perform tasks.

The application 20 also may include the functionality to simultaneously market customized, experience-rated client RFPs to a plurality of benefit providers for multiple benefit products and services. A system-generated, customizable client proposal and presentation format may be produced and presented to the client by the benefit broker/consultant providing information regarding responses to the RFP from a plurality of benefit providers. In addition, the application 20 may train benefit broker/consultants, and their employees, on benefit products and services through the user of customizable plan templates with tutorials, built-in user intelligence and customer analytics.

One exemplary embodiment of functionality of the application 20 and/or design method 10, shown generally in FIG. 1A, shall be described with reference to FIGS. 2-7. When considering this exemplary functional embodiment, as exemplified in detail in the flow diagrams of the figures, and which may at least partially be described elsewhere herein, the primary users of the application 20 include benefit broker/consultants, employer/clients, employees, benefit providers, and application administrators. With proper authority and access provided as described herein, such users may access the application 20 via one or more portals including the application administrator portal 22, the benefit provider portal 26, the benefit broker/consultant portal 24, the employer/client portal 28, or the employee portal 30.

The overall functionality of the application 20 may be divided into one or more areas of functionality including one or more of the following: employer benefit management, agency/enterprise management, ancillary business/enterprise applications, application administration, and user administration. Such areas of functionality preferably account for at least certain business processes inherent within the benefit supply chain. Several of such processes are described below.

An employer/employee demographic process area pertains to the creation of employer and employee demographic information (e.g., census information). For example, the user may manually enter or import the required data or information into the application 20.

A plan design process area pertains to the design of a specific benefit plan. For example, the benefit broker/consultant may design a plan in conjunction with the employer. The design may include taking a plan template, e.g., an empty or partially populated master product template and filling in the required details for the product, or include selecting a standard plan. The design can then be marketed internally (e.g., at the benefit broker/consultant by the application 20 or externally apart from the application by one or more benefit providers).

An external benefit marketing process area pertains to the external marketing of a benefit plan. For example, the external marketing process may include the creation of a RFP and the negotiation of benefit provider responses. These responses may be assembled into a client proposal in a benefit selection process area.

An internal benefit marketing process area pertains to the internal marketing of a plan. For example, if an employer is qualified for a standard plan, a rate calculation engine (e.g., as part of the application 20) may be used to provide standard plan responses. These standard plan responses may be assembled into a client proposal in a benefit selection process area.

A client proposal process area pertains to the creation of client proposals after responses to RFPs have been received. For example, a customized client proposal may be developed using system-generated master client proposal templates, e.g., templates that may be populated by RFP response information from one or more benefit providers.

A plan selection process area pertains to the employer selection of a benefit plan. For example, the benefit selection process may begin with the benefit broker/consultant creating a client proposal from various internal and external marketing responses. The employer/client may then determine which plan(s) to select. This selection may then be installed in a plan installation process area.

The plan installation process area pertains to the installation of a benefit plan. For example, the plan installation process may include the employer completing a benefit provider's application, the selection of plan(s) by the employer and the employees, and the forwarding of the selections to the benefit providers. Generally, plan enrollment is a HIPAA regulated activity and this functional process is preferably HIPAA compliant.

A plan administration process area pertains to the administration of a benefit plan. For example, benefit administration may include the ongoing process of communicating plan enrollment data driven by census changes to the benefit providers for calculating premium remittance statements.

A plan amendments process area pertains to making amendments to a benefit plan. For example, this may involve the process specific to making contract changes to an inforce plan contract (e.g., a current benefit plan that has been adopted) during the plan policy year.

A plan renewal process area pertains to the renewal of benefit plans prior to, or after, expiration of the benefit plan; preferably, prior to expiration. For example, this may involve processes specific to preparing new inforce plan rates for the upcoming plan policy year and/or the analytical activities associated with proposed renewal rates.

A plan communication process area pertains to the providing go information regarding the benefit plan to employees. For example, summary plan descriptions, provider specific claim forms, a benefit provider reference library, and an employee health care planner may all be communications between the employer and the employees.

Another process area may pertain to providing premium reconciliation and remittance statements. For example, this may be beneficial when a user selects to generate a plan remittance statement (e.g., a report) associated with employee demographic and plan rate information.

A data mining and reporting process area generally pertains to the various types of reporting the system provides. For example, the employer benefit management reporting tools and templates may be used to generate unformatted reports (e.g., custom reports where the user selects the fields and the order in which they are to be presented) and formatted reports (e.g., preset formats that cannot be customized by the user).

A benefit management services process may include, for example, various fee-based benefit management services to which a benefit broker/consultant (or an employer who is not using a benefit broker/consultant) can subscribe. For example, these services may consolidate and streamline a number of administrative service functions that are normally outsourced to a variety of service providers. For example, these services include ERISA reporting, group life tax reporting, ID card generation, medical reimbursement administration, retirement planning, Section 125 (cafeteria plan) administration, benefit notification and/or continuation (e.g., COBRA) and transitional benefit coverage (e.g., individual plan coverage).

An agency/enterprise management process area pertains to the management of a benefit consulting firm or agency. For example, agency management may include maintaining license and appointment information (e.g., calendaring functions, such as the mapping of activities, such as appointments and critical dates, to particular clients), maintaining client/provider contact information, and administering commissions and bonuses, etc.

An application administration process area pertains to the management of the application 20. For example, application administration may include maintaining coded list tables, maintaining the standard plans, maintaining the rate calculation engine, maintaining panels or templates, etc.

A user administration process area pertains to the administration of the users of the application 20. For example, user administration includes adding and authorizing users, and customizing the user portals (e.g., allowing users to access certain panels or templates and/or certain data that populates certain panels). Further, for example, a login and authentication process area may provide login and authentication processes. For example, every user of the system may be logged into a portal. Further, for example, the functionality available to a user will be dictated by the authorizations available to them during this login process.

Figure 7:
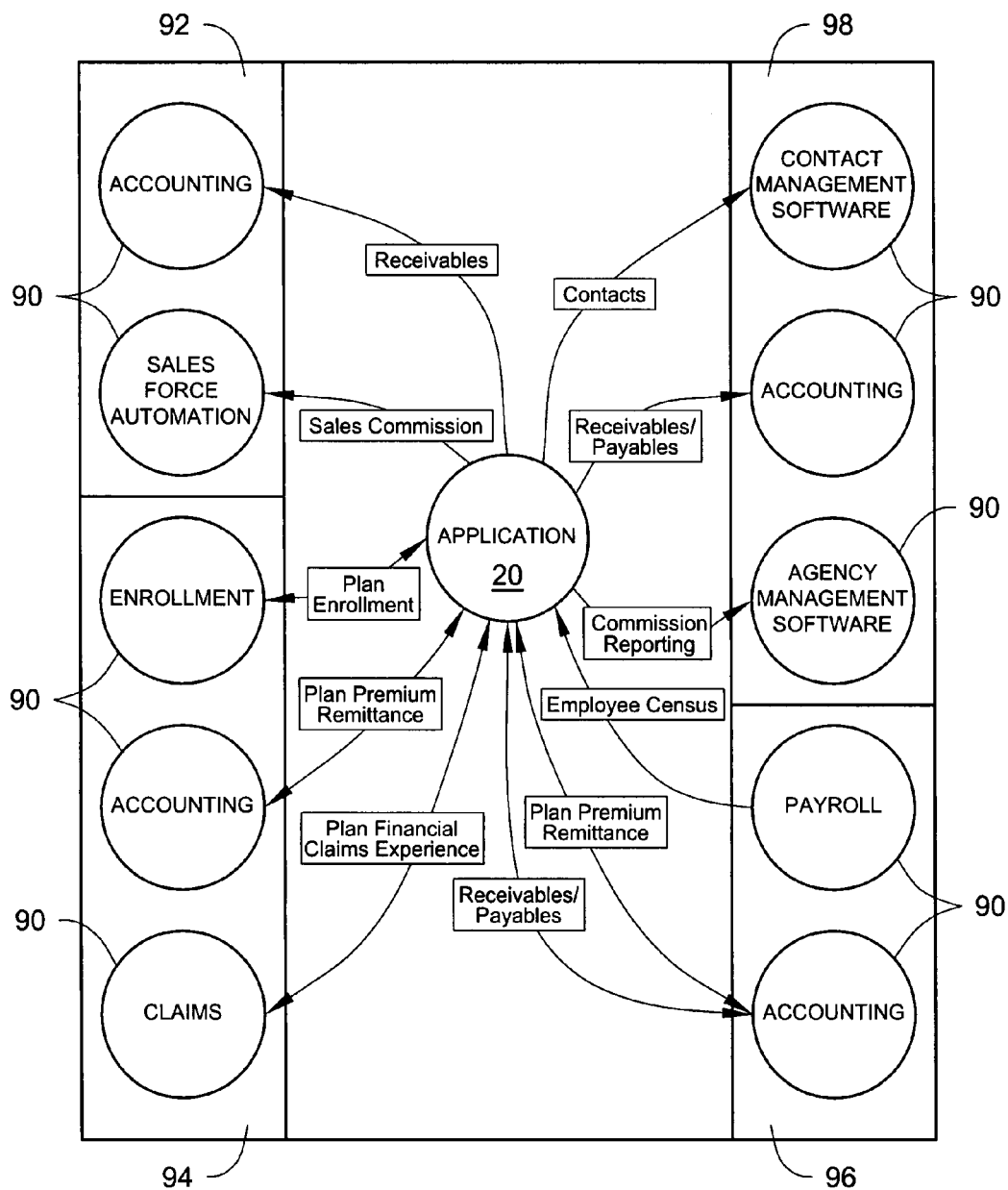
FIG. 7 is a general diagram illustrating ancillary applications that may be used in combination with functionality as shown generally in FIG. 1A according to the present invention.

An internal systems process area pertains to interfaces that allow for the communication between the application 20 and internal software systems of one or more users. For example, FIG. 7 shows the context of the application 20 with regard to other software ancillary systems 60. For example, each block in FIG. 7 describes the environment of a user of the application 20. For example, block 92 represents the application administrator environment, block 94 represents the benefit provider environment, block 96 represents the employer/client environment, and block 98 represents the benefit broker/consultant environment. Each circle 90 represents a software system within the environment, with the central circle representing the application 20. Each arrow represents the flow of information, with double-headed arrows indicating that information may move bi-directionally between the software systems. For example, such information flows may include one or more of the information flows described below.

For example, client billing and receivables information may flow between the application 20 and the accounting systems of the administrator, the benefit broker/consultant, the employer/client, and/or benefit providers. It may, for example, contain the financial records of receivables and payables gathered by the system. Payment of these payables and receipt of the receivables may be handled by electronic funds transfer as a separate activity.

Sales commission information may flow, for example, between the application 20 and a sales force automation tool. Commission may be the sales compensation paid to the sales staff.

Plan enrollment is preferably a HIPAA compliant message that contains new plan enrollments, terminations and changes to enrollment with the benefit provider. The provider may acknowledge these messages according to the HIPAA regulations. This may include viewing plan enrollment as well as creating employee enrollment.

A client premium remittance statement may also be information that flows. For example, the benefit broker/consultant may use tools and templates to generate a monthly employer/client remittance statement.

Plan financial record information flow may be enabled when a user selects to import plan financial experience report data files from a benefit provider. These reports could include employer summary level information or employee level claims detail.

Contact management information flow may carry contact information between the application and benefit broker/consultant's contact management software. The application 20 may contain provider contact management templates.

A plan provider commission report may also be provided. The application 20 may provide tools to forecast and track benefit provider commission payments on a benefit plan basis. The commission report will be derived from the plan rates, the employee/dependent enrollment, and the type or amount of benefit factored by a commission formula.

Further, employee census information flow may carry the employee data from the employer payroll system to the application.

Figure 2A:
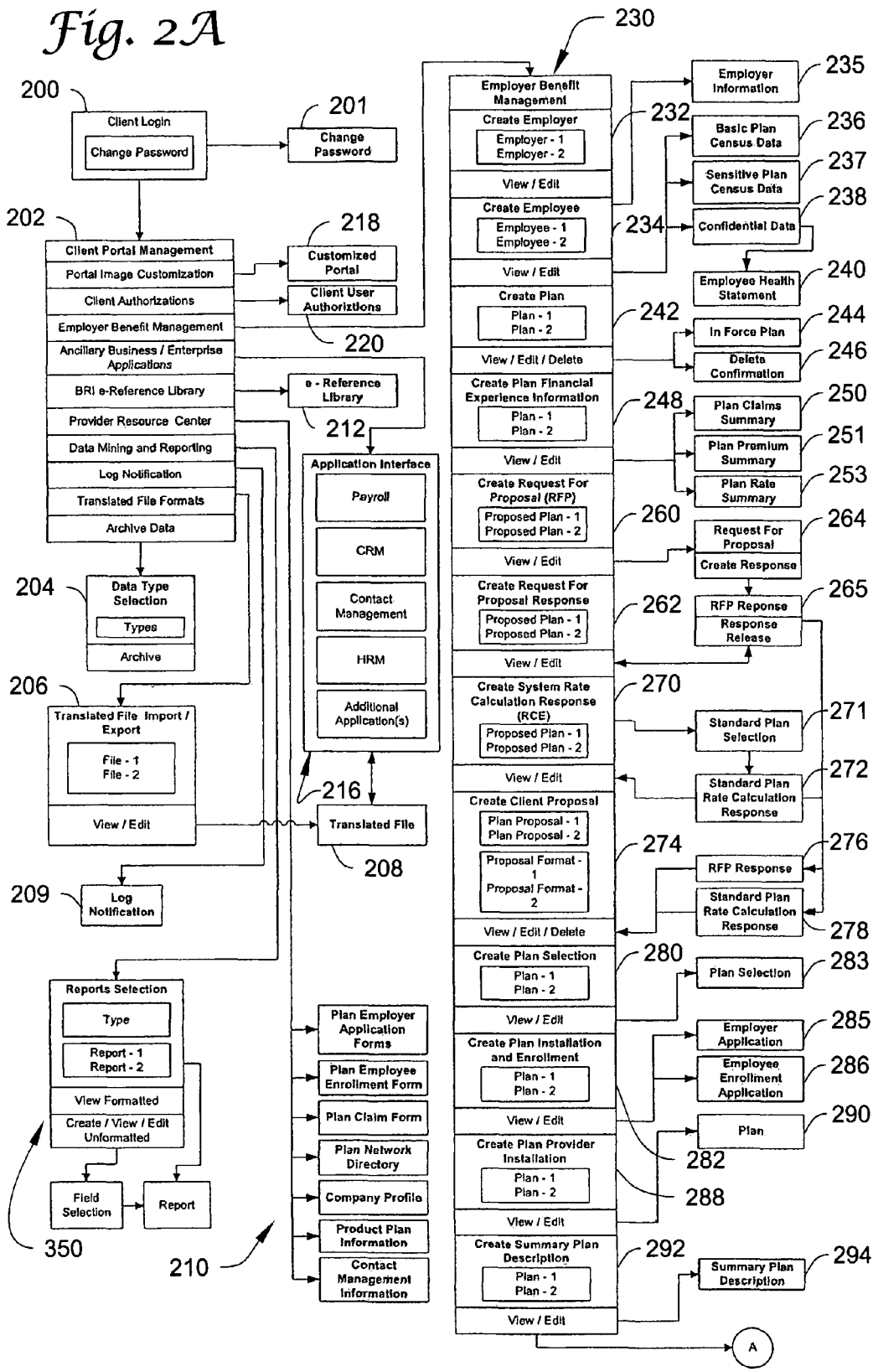
FIGS. 2A-2B (hereinafter referred to herein as FIG. 2) is a general flow diagram showing functionality shown in FIG. 1A that may be accessible through a portal by a client of the application administrator, such as, for example, a benefit broker/consultant (e.g., a benefit broker or a broker firm) and/or an employer/client according to one embodiment of the present invention.
Figure 2B:
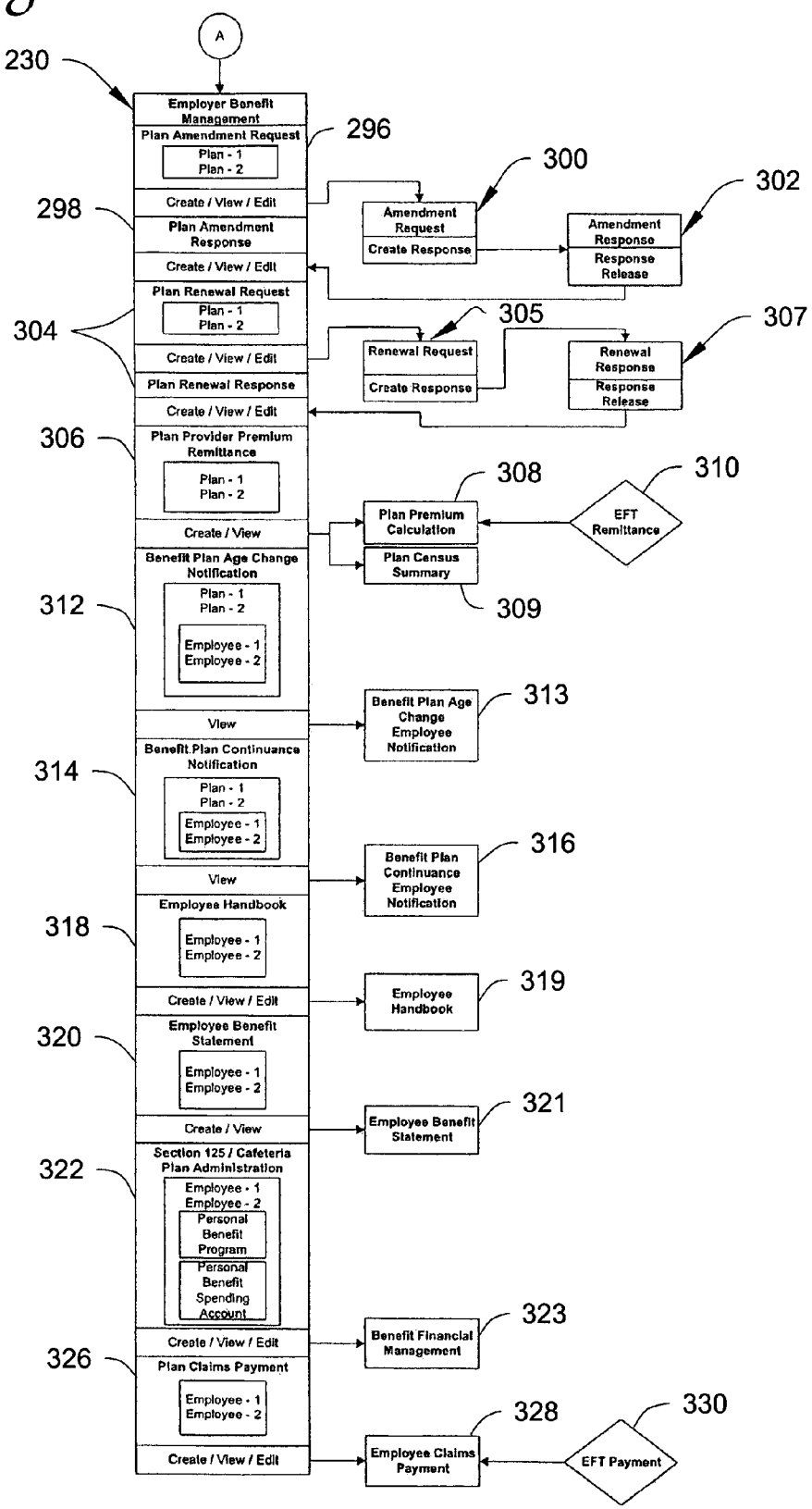
Figure 3A:
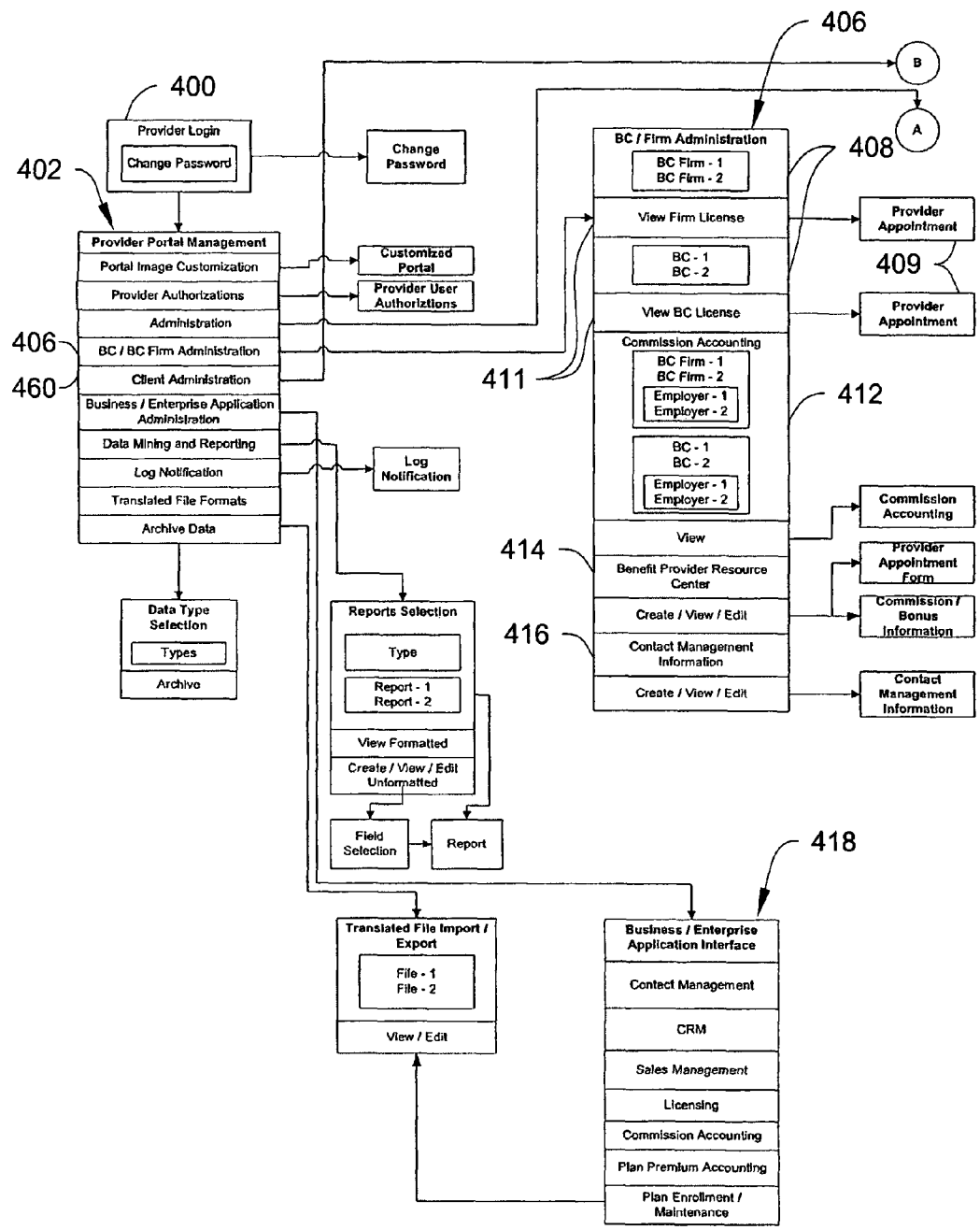
FIGS. 3A-3C (hereinafter referred to herein as FIG. 3) is a general flow diagram showing functionality shown generally in FIG. 1A that may be accessible to a benefit provider through a portal according to one embodiment of the present invention.
Figure 3B:
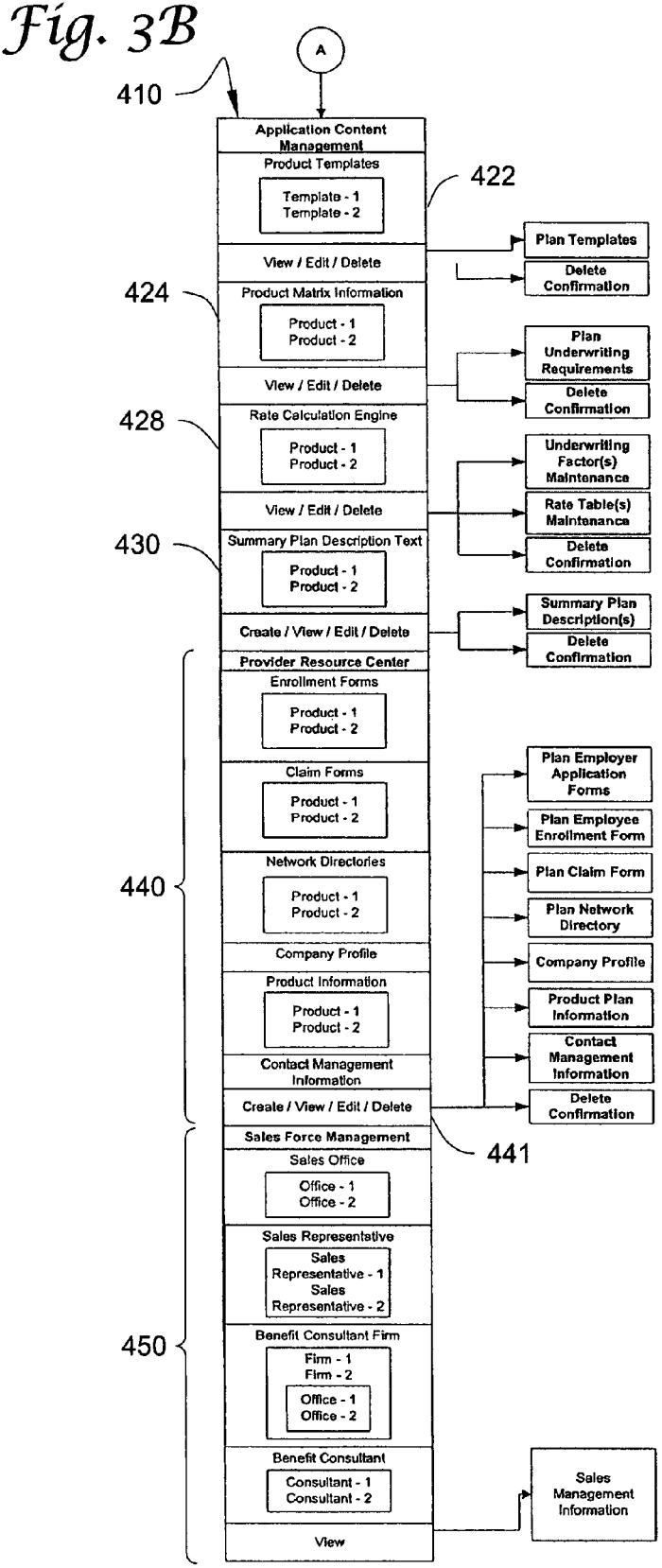
Figure 3C:
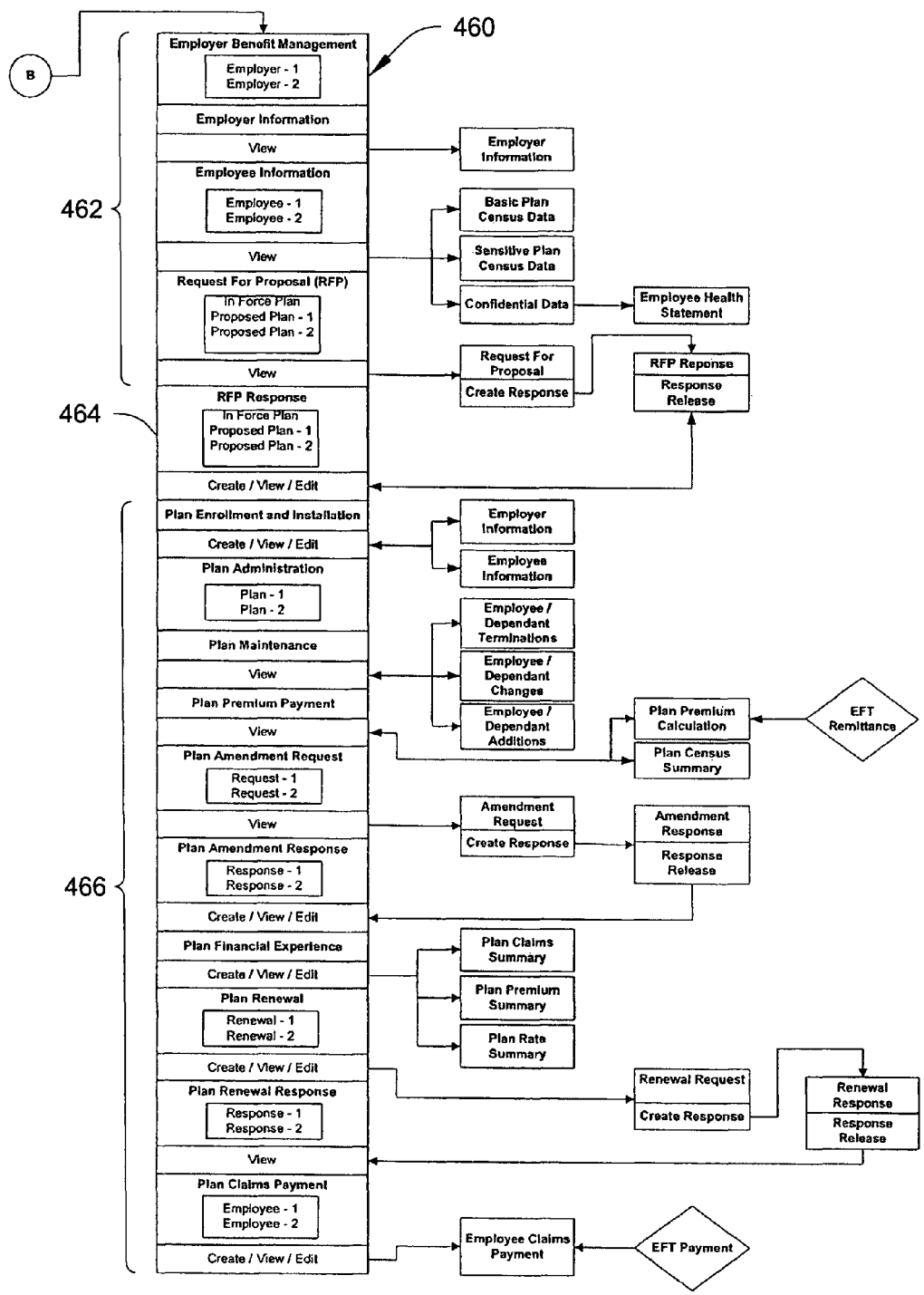
Figure 4:
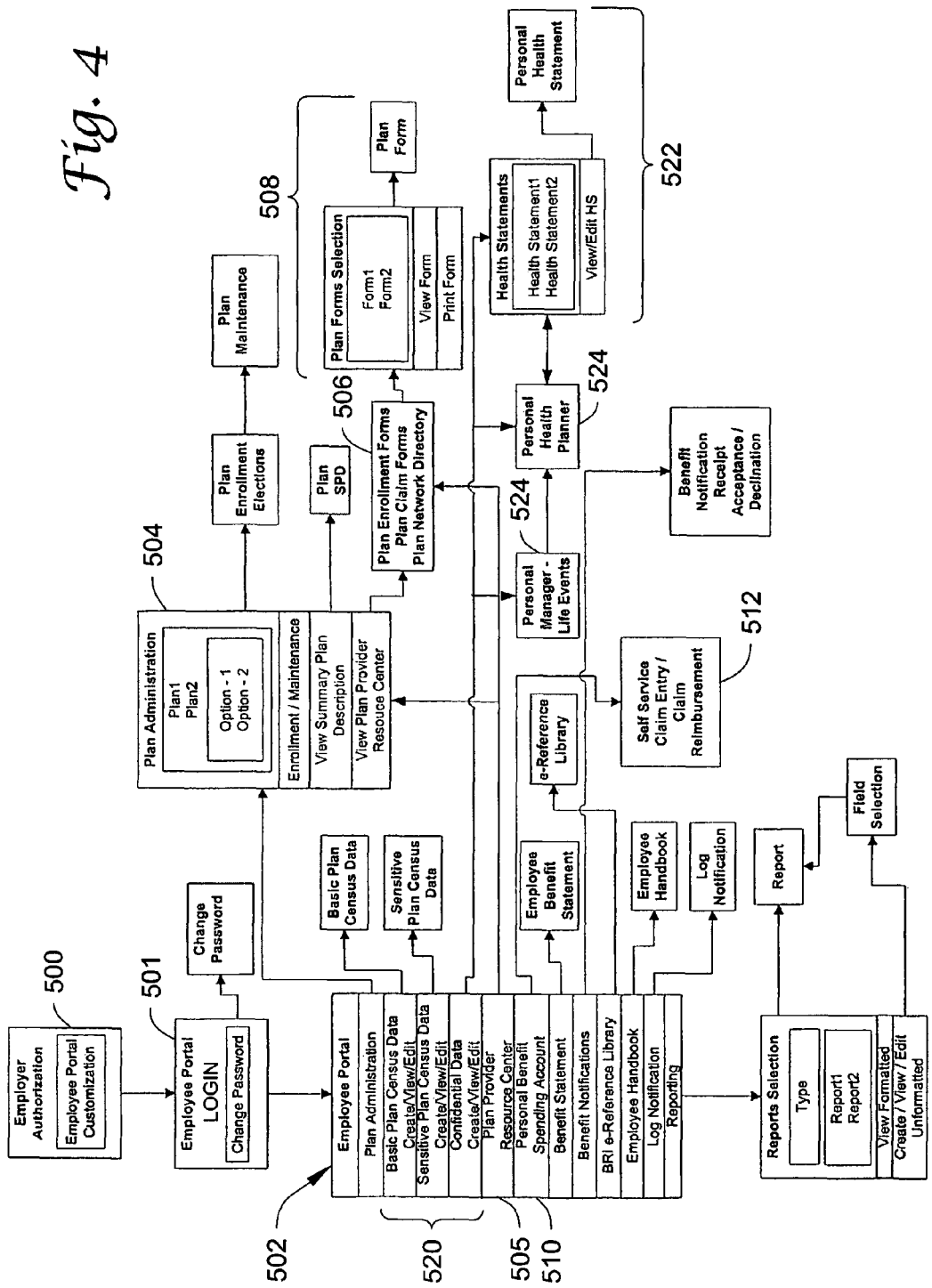
FIG. 4 (hereinafter referred to herein as FIG. 4) is a general flow diagram showing functionality shown generally in FIG. 1A that may be accessible to an employee through a portal according to one embodiment of the present invention.
Figure 5A:
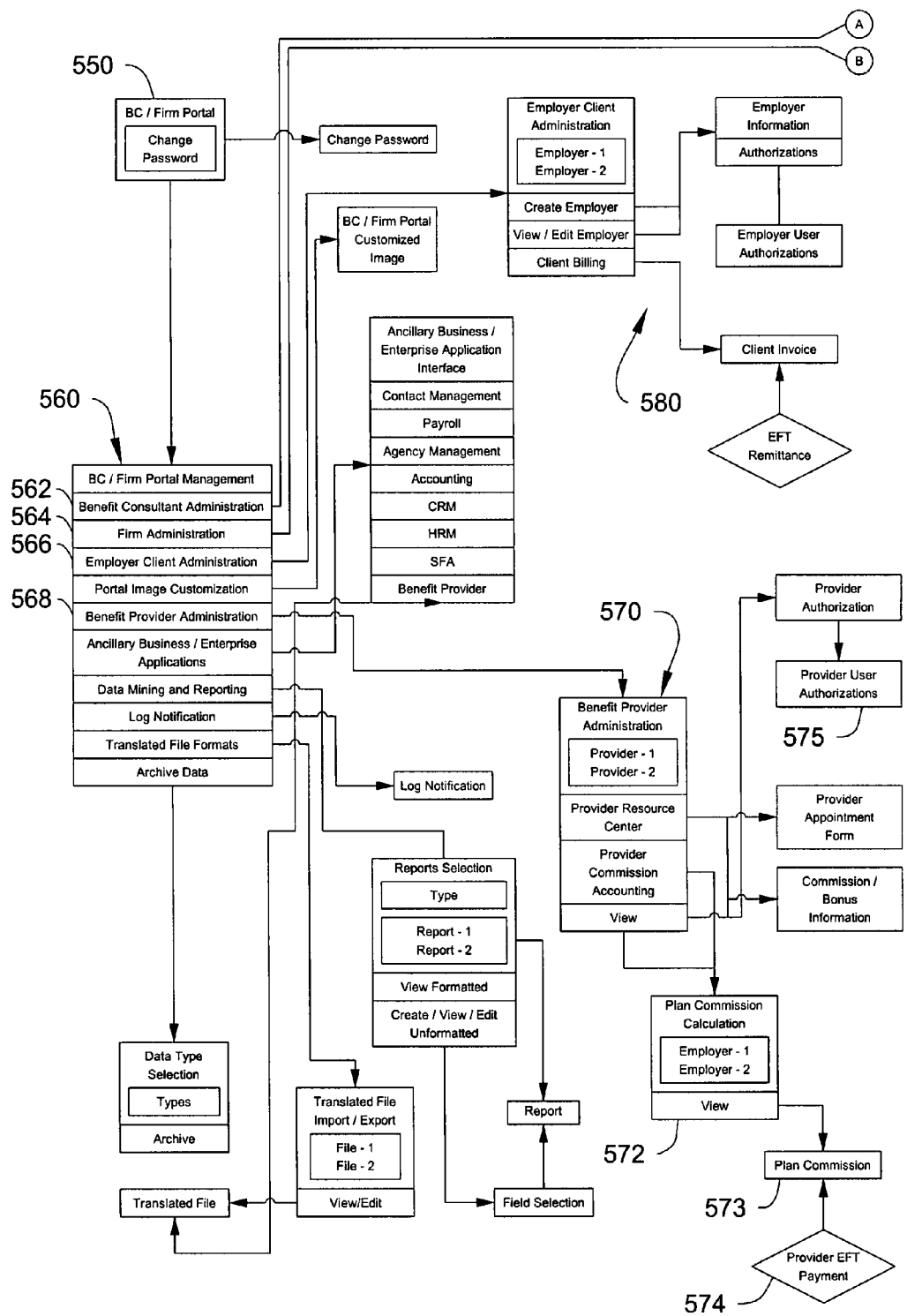
FIG. 5A-5B (hereinafter referred to herein as FIG. 5) is a general flow diagram showing functionality shown generally in FIG. 1A that may be accessible to a benefit broker or firm of more than one benefit brokers according to one embodiment of the present invention.
Figure 5B:
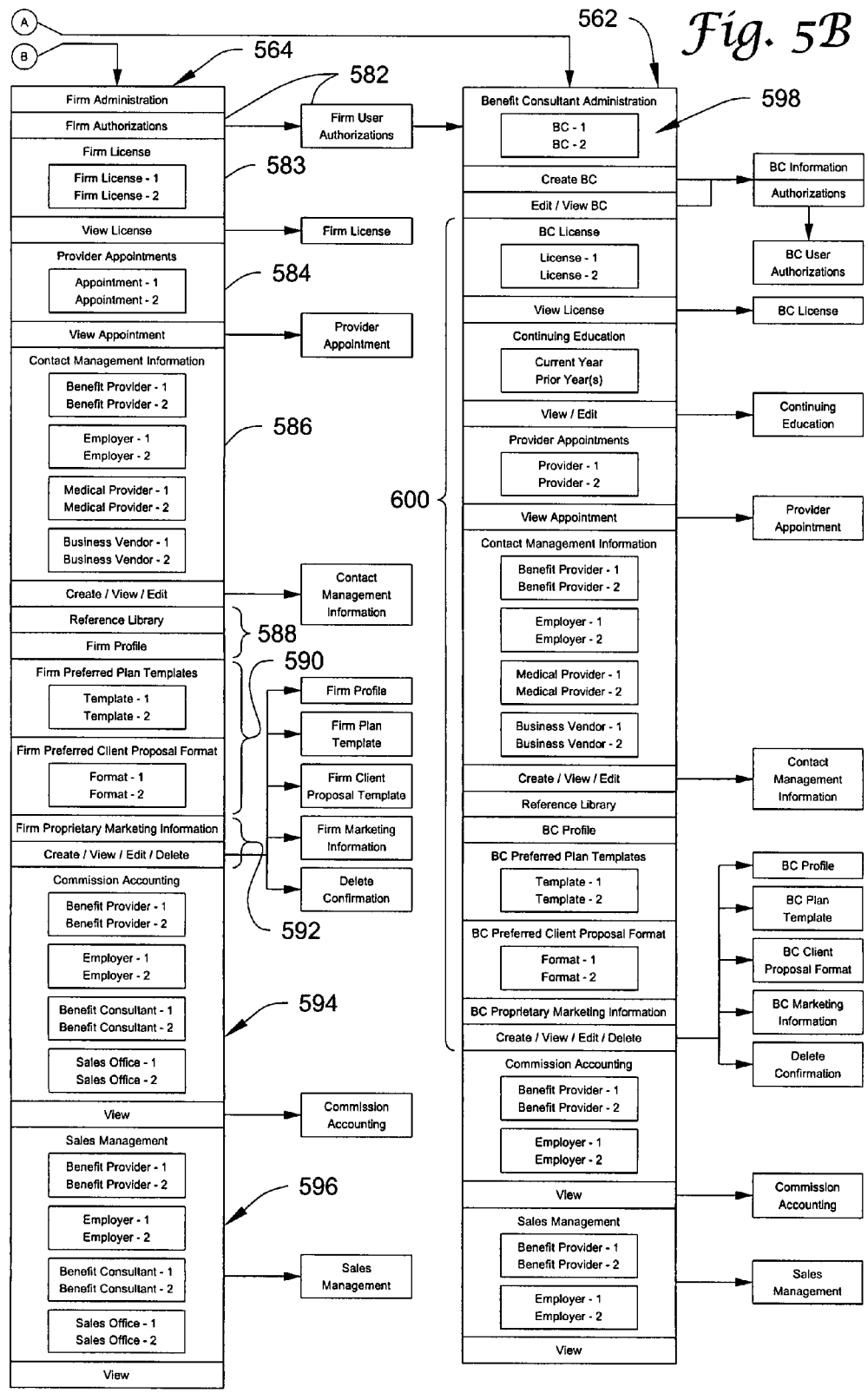
Figure 6:
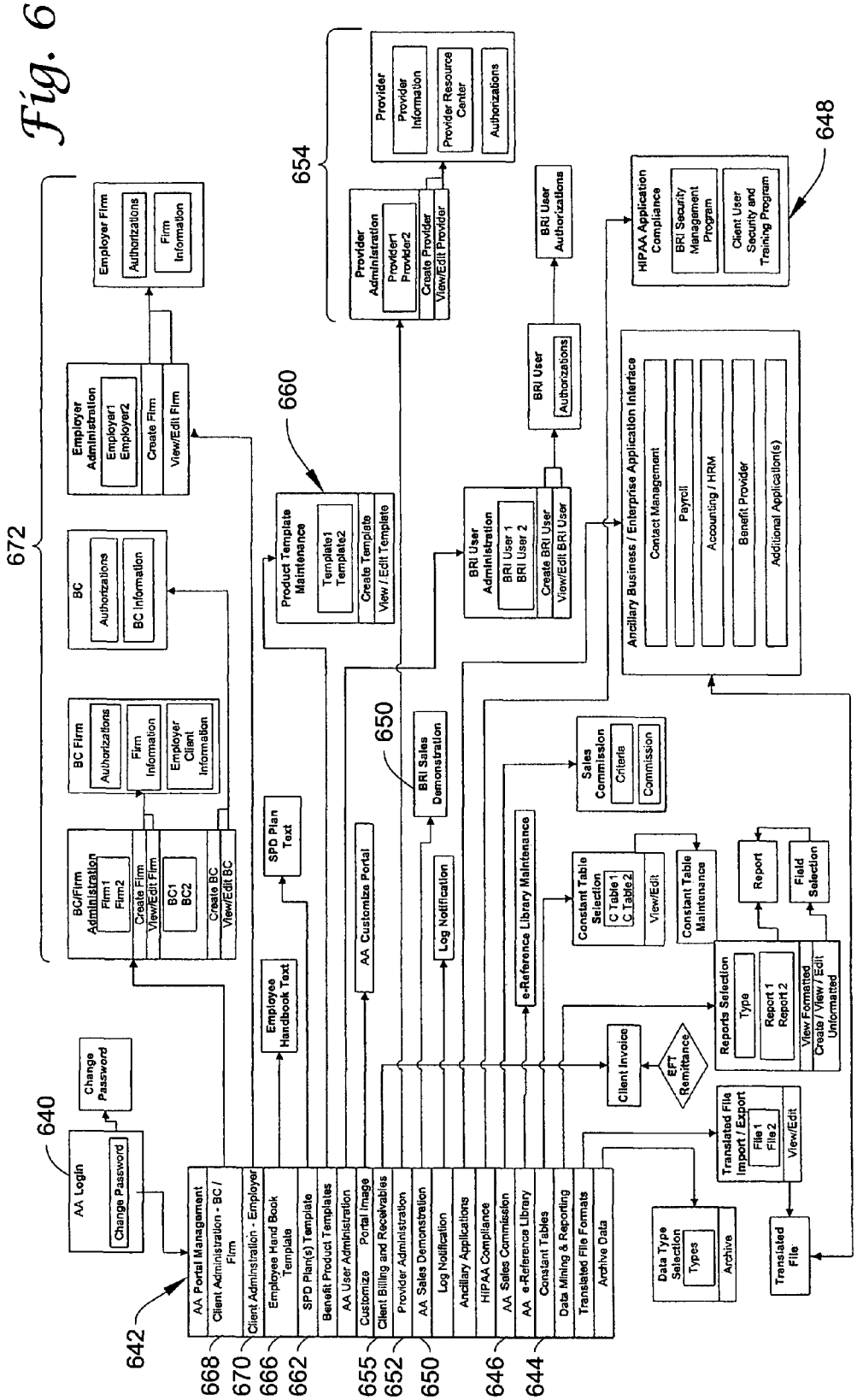
Figure 6 is a general flow diagram showing functionality shown generally in FIG. 1A that may be accessible to an application administrator through a portal according to one embodiment of the present invention.

The flow diagrams shown in FIGS. 2-6 are representative of application functionality (e.g., functionality for implementing one or more process described above such as the RFP process, the client proposal process, etc.) that may be accessed by one or more users according to one exemplary embodiment of the present invention. For example, preferably, FIG. 2 shows functionality that may be accessed by a benefit broker/consultant (e.g., benefit broker/consultant firm or a single benefit broker/consultant) or may be accessed by an employer/client, depending upon the role taken by the user in the overall benefit plan system. FIG. 3, for example, describes functionality that may be accessible by a benefit provider through a benefit provider portal. Further, FIG. 4 shows a flow diagram of functionality that may be accessible to an employee having access through an employee portal to the application 20 of the benefit management system. FIG. 5, for example, preferably shows agency/enterprise management functionality accessible to a benefit broker/consultant through a benefit broker/consultant portal to the application. Further, for example, FIG. 6 shows a flow diagram of the functionality accessible to an application administrator through an application administrator portal in one exemplary embodiment of the present invention.

For example, as shown in the general embodiment of FIG. 1A, the functionality shown in the flow diagram of FIG. 6 may be accessible to the application administrator through the application administrator portal 22. The functionality shown in the flow diagram of FIG. 2 may be accessible through the benefit broker/consultant portal 24 by a benefit consultant or a benefit consultant firm as the user of the application 20, or, likewise, an employer user may have access to such functionality through employer/client portal 28, as shown in FIG. 1A. Likewise, the functionality shown in the flow diagram of FIG. 3 may be accessible by a benefit provider through the benefit provider portal 26 as shown in FIG. 1A; the employee user may have access to the functionality shown in FIG. 4 through the employee portal 30 as shown in FIG. 1A; and a benefit broker/consultant such as a benefit consultant or a benefit consultant firm may have access to the agency/enterprise management functionality shown in the flow diagram of FIG. 5 through the benefit broker/consultant portal 24.

As shown in the flow diagram of FIG. 2, a user, referred to in the diagram as a client (e.g., a benefit consultant, benefit consultant firm, or employer which may be a client of the application owner/administrator), may upon login 200 change a password or perform one or more other client portal management functions. For example, as shown in block 202, the user may perform portal image customization, client authorizations, employer benefit management functionality, ancillary business/enterprise application functionality, access an e-reference library, access a benefit provider resource center, perform data mining and reporting, log notification, translate file formats, and/or archive data.

Archiving data functionality is shown in further detail in block 204, wherein certain data types may be selected and archived.

Translation of file formats is shown in further detail in block 206. For example, various files may be imported and/or exported to provide information into the system or provide information to other systems. Such files may be viewed and edited, and the translated file may be used for one or more purposes such as translated file 208, which is shown as being provided to the application interface for use by one or more ancillary applications as previously described herein.

Log notification refers to the logging, e.g., recording by the system, of an activity performed by a user. Generally, the system provides a user with notification that the activity has been logged into the system, e.g., type of activity, time, date, etc.

The resource center of a benefit provider is shown in further detail in blocks 210. The benefit provider may provide various available information for access by one or more users (e.g., employees, employers, benefit consultants, etc.). For example, the benefit provider resource center may include benefit plan employer application forms, benefit plan employee enrollment forms, benefit plan claim forms, a benefit plan network directory, a benefit provider company profile, product plan information, and contact management information. Such a resource center is not limited to only such information but may include any other information that may be beneficial to a user of the present invention.

An e-reference library 212 may also be provided to the user. The user may thus access various internet sites to obtain information. For example, a benefit consultant may wish to access a state licensing agency to obtain necessary requirement information to maintain licensure.

Ancillary business/enterprise applications may also be accessed by the user. Such applications may include those shown in the application interface 216 of FIG. 2. Such ancillary applications have been described previously with respect to FIG. 7 and may include payroll applications, customer relationship management (CRM) functionality, contact management functionality, human resource management (HRM) functionality, as well as one or more other additional applications.

The present invention is designed to be an open business application allowing for efficient integration with other business or ancillary applications. Tight integration, using interfaces, allows the application to move data, for example, import/export data, e.g., using translated files of import/export functionality 206, to/from other ancillary applications. For example, tight integration may be used to move data to and from payroll as well as other management applications. Further, loose integration may be used with various other ancillary applications such as ancillary accounting applications, CRM applications, HRM applications, as well as sales force applications.

For example, with respect to exporting a file to an integrated application, a user may select to export data from an interface of the application 20 to an integrated application. For example, the system may display a listing of integrated applications. The user may select an application to receive the data file and, upon prompting, the user may specify the type of data. The user then may specify the type of data and select it to export the data. Thereafter, the system exports the data to the selected application and logs the activity providing a log notification to the user (e.g., using log notification functionality 209). Data file imports from an integrated application would be provided in much the same manner, as well as imports and exports from non-integrated applications.

A portal allowing access to one or more functions of the application 20, or a user interface thereof, may be branded or image customized by the user resulting in a customized portal 218. The functionality of such branding of the portals is described elsewhere herein and, as such, shall not be further described with reference to FIG. 2.

Client authorization functionality is also provided to the user. For example, the user may extend authorization to one or more employees, employers, etc., to have access to one or more functionalities provided by the application. For example, a benefit consultant firm may give one or more benefit consultants working for the firm access to employer benefit management functions, as shall be described further herein. As is described herein with reference to the system architecture, a client authorized to access the application (e.g., a client having a particular role and an ability to perform one or more various tasks) may extend such authorization to others such that they may perform such roles or tasks, e.g., by extending a portal to such individuals or users. For example, extending satellite sites to a child portal may be one method of extending such access to other individuals, as is described herein with respect to the application architecture 12 as shown generally in FIG. 1A. Such processes generally result in client user authorizations 220 being extended to one or more other users.

The remainder of the description of the flow functionality of FIG. 2 shall primarily be described with reference to a benefit broker/consultant as a user of the employer benefit management functionality 230. The employer benefit management functionality 230 allows for a plurality of processes to be carried out (e.g., census data creation, plan creation, plan amendment, etc.).

A record for one or more employer/clients of the benefit broker/consultant may be created (block 232). For example, the benefit broker/consultant may select to create an employer record. The system may then retrieve employer/client information templates or panels that require the entry of various types of information 235 such as employer demographic information, employee/dependent demographic information (e.g., census information), planned financial experience information such as current plan and historical plan policy year information including rates, prepaid premiums, and paid claims summary data. After the user enters the employer information 235, the system may verify that the user has entered the required data or notifies the user if required data still needs to be entered. The employer information then may be saved by the user and the system saves and logs the information. It will be recognized that one or more employer/clients may be created by the benefit broker/consultant. Such employer information in the record may be edited and viewed as required by the user with the changes being logged.

Further, the creation of employee records may be performed (block 234) using similar selection and entry of various types of employee demographic information. For example, such demographic information may include basic information 236 such as standard census information including name, date of birth, date of hire, and sex. Further, more sensitive information 237 such as social security number, salary, job title, job class, employment status, may also be entered. Likewise, confidential information 238 such as HIPAA protected information, including personal health plan information, personal health statements 240, personal manager, personal medical records for the employee and/or dependents thereof, and personal claim summaries of information of employees and/or dependents, may also be provided in the employee demographic information.

Various methods may be used to record information, such as basic and sensitive information, including the importation of such basic/sensitive employee census data from payroll. In other words, a payroll system may be tightly integrated with the application for bulk loading of employee information. Further, for example, a spreadsheet format, e.g., such as an Excel spreadsheet, may be utilized that includes the employee data and which can be used in a bulk data import. Lastly, for example, the employee census data may be manually entered using a template or panel presented in an interface to the user.

Some information, such as confidential employee demographic information which requires a higher degree of security, may be limited in the manner of entry. For example, such information may be only allowed to be loaded by manual data entry to enhance security associated therewith.

An employee edit and view function may be used to update and revise employee/dependent demographic information (e.g., census maintenance). Such information may be used by plan creation process and may include one or more of the following maintenance changes: employee plan enrollment, employee plan termination, marital status change, name change, address change, dependent status change, salary change, job class change, employment status change, beneficiary designation change, and/or employer location/demographic changes.

It will be recognized that the benefit consultant may authorize access to various other users for maintenance purposes. For example, the benefit broker/consultant may authorize or extend access to make changes to employee demographic information to an employer/client (e.g., a satellite site), with the employer/client extending access to an employee to make one or more changes in the information (e.g., a child portal). One will recognize that such access may be to all of the basic, sensitive, and confidential information or, for example, may be limited to only basic and sensitive information access.

The flexibility of using satellite and child portals with extended user role and task access defined by user specifications of user names and/or passwords, etc., allows for one or more administrators in the benefit chain to define and provide a way for tasks to be performed at the lowest level. In other words, if a task can be performed by an employee as opposed to having to be performed by an employer or the benefit consultant, then an employee should be allowed to have access and perform such a task. For example, such tasks may involve employee demographic changes or dependent status changes, as well as access to benefit provider information to view selected coverage.

One will recognize that various levels and types of user access may be defined according to the present invention, and those presented above are merely exemplary of the extensions of user access, e.g., via satellite sites and child portals, that can be provided according to the present invention.

Plan creation functionality 242 allows a user to create or record a benefit plan using either an empty template, e.g., a master product template, or a standard template. A plan template is generally characterized as a tool for electronic data capture and storage of one or more different types of benefit plan information (e.g., demographic data) and/or plan provider information (e.g., detailed written contract information between an employer and an insurance provider).

For example, the user may select to create a plan using a master product template from a list of available templates. The system retrieves and displays the template in a user interface and the user manually configures and enters the plan details and selects to save the plan assigning it a status, e.g., a status such as a plan inforce, a proposed plan, or a historical plan. As usual, the system saves the plan and logs the activities performed by the user.

The benefit plan may also be created by using a template created by the benefit broker/consultant from a benefit broker/consultant plan reference library available to the user. Likewise, one or more standard plans may be designed and be selected by a user, wherein the user can manually enter the plan details into a standard plan. As shown in FIG. 2, an inforce plan 244 may be selected and scrapped (e.g., deleted and confirmed) (blocks 244 and 246), with a new plan to be created. Further, editing of the plan and changing thereof may occur.

An appended plan may also be created, which is a type of proposed plan. Such terminology is used for a plan that has been chosen as the new plan but is not yet inforce. When changing the plan status type of a plan inforce or a proposed plan to terminate it, the user may select where to file the terminated version of the plan. A terminated inforce plan may be filed separately from a terminated proposed plan. The terminated plan may also be filed in a historical folder and/or archive folder for later use. A deleted plan can be any plan for which the user has no future use. For example, the user must have authorization to purge a plan from the application.

Plan financial experience information records may also be created (block 248). Such information may be input manually or may be imported plan financial experience data files, e.g., data files from a benefit provider. For example, the reports could include employer/client summary level information or employee level claims detail such as plan claim summary 250, plan premium summary 251, and plan rate summary 253. Such information may be edited and viewed by a user.

In at least one embodiment, a marketing cycle is begun with the creation of a benefit plan design, e.g., such as a benefit plan design created as described above using a standard or master template, and the recording of employer demographic information and employee/dependent demographic information (e.g., census information). With the creation of a benefit plan, whether proposed, currently inforce, and possibly edited, or with regard to any other type of benefit plan, the plan may be processed internally by a rate calculation engine 270 using the employer/client demographic information to generate a plan response and/or an external market search may be conducted from the same plan design.

For example, a request for proposal (RFP) can be generated (block 260) and transmitted to selected benefit providers in anticipation of a response therefrom based on the RFP (block 264). Such an external market search may involve designing and releasing the RFP to a selected one or more benefit providers in the form of a customized request for RFP response (block 262) in anticipation of getting a response therefrom (block 264).

The request for RFP response functionality (block 262), at least in one embodiment of the present invention, provides for the grouping of reports developed by the application through the use of data input templates or panels. For example, one or more of such reports may include employer demographic information, master employee census listing information, personal health statements, benefit plan designs, and benefit plan financial experience information. In other words, information needed by the benefit provider to provide a response 265 to the RFP is provided in a package such that it can be provided to a benefit provider in an anticipated response therefrom.

For example, a graphical user interface may allow a user to select and market the employer/client's plan design by displaying a window to enter the employer/client's name and a listing of the employer/client's plans. The user may enter the name and select the plans to market. Various RFP report templates may be provided with the system populating the RFP report templates. The system may save the RFP report and associate it with the proposed plan. Thereafter, the user may, for example, select to release the RFP to a selected number of perspective benefit providers. The system then releases the RFP with notification (e.g., an e-mail notification) to one or more selected benefit providers and logs and tracks the RFP and the benefit provider responses.

The RFP may be tracked by the system for receipt verification, notes and messages between the users, and receipt of benefit provider RFP responses thereto. For example, the employer/client may be given an option to view various plans which have been sent as part of a RFP and display tracking information with regard to whether responses to the RFPs have been received.

A RFP response is generally created by the benefit provider. For example, a benefit provider may prepare and release their response to a RFP (block 265). For example, the benefit provider may select a RFP to be responded to from a display listing a plurality of RFPs. The system may display a listing of employer/client plan information templates requesting the response to a RFP. A benefit provider may review and analyze the information and create notes, records, and e-mails for their proposed response. A line-by-line response to the plan specifications and calculated rates in a provider RFP response section of the benefit plan template may be used by the benefit provider. The RFP response may then be provided back to the application for access by one or more other authorized users. The user, such as a benefit broker/consultant or employer/client, may view the provided RFP response via a user interface.

As opposed to an external system market search for responding to a RFP, an internal system rate calculation engine (RCE) may be used to create a RFP response (block 270). Such a rate calculation engine may include one or more algorithms to provide a response from the information populating the RFP. For example, a user may select to request a system generated RCE response 272. Typically, such a response would only be allowed for a standard plan 271 selection where quotes from one or more benefit providers (e.g., rate information or rate algorithms) have already been provided by the benefit provider.

For example, the system may display a listing of standard benefit products and the user may select a product from the standard listing along with a plan design associated therewith. The system may then display a listing of benefit providers that support this standard plan. The user may select one or more of such benefit providers, and the system may generate a listing of standard plan proposal response report templates. The user may then select a particular template to be populated by the system. The system prepares the RCE response reports and notifies the user of such preparation. The user then receives the RCE standard plan response reports. Using standardized plans and the RCE to prepare a response will most likely shorten the time for access to a RCE response. The RCE response may then be viewed by the user. Such a RCE response may include quotes from a plurality of benefit providers for the same standardized plan.

A client proposal report may then be created using the functionality of block 274. In other words, one or more RFP responses 276 or standard plan RCE responses 278 may have been received for one or more benefit plans created by the benefit consultant for a particular employer/client. The create client proposal functionality 274 would allow the aggregation of such responses into a client proposal template that may include, for instance, a cover letter, an image-branded, customized client proposal cover page, a table of contents, benefit consultant and/or firm profile information, plan contract comparisons, benefit plan rate comparisons, benefit plan summaries, benefit plan highlights, employer cost summaries, employee cost summaries, benefit provider company and product information, and graphic analysis and illustrations to support any one or more of the above or to provide additional information. It will be recognized that the user creating the client proposal may view and edit different versions thereof and/or select RFP responses to be used therein. All of such functionality may be provided via a user interface, for example, which presents RFP response information to, for example, a benefit broker/consultant for compiling such a client proposal.

With the client proposal functionality providing a report in one or more different proposal formats (block 274), a plan may be selected (block 280). For example, the user may select to accept a proposed plan by selecting a displayed list of provider proposal responses with the user selecting one of the proposal responses to be used as the selected benefit plan, as shown generally in block 283.

Plan installation and enrollment functionality 282 results in the selected plan (e.g., an appended plan) becoming the employer/client benefit plan that is inforce. For example, employer/client plan installation templates (e.g., employer application 285) and provider reports including, for example, the preliminary application of group insurance, first month deposit premium payment, most recent wage and tax statement, prior carrier's master group policy, master employee plan listing, employee/dependent deductible credit/carryover listing, plan provider termination notification, and any other information may be provided for population thereof. Further, employee plan enrollment templates and provider reports (e.g., applications 286) such as, for example, employee enrollment forms, personal health statements, etc., may be provided for population.

Plan enrollment is the process by which the benefit plan provider is notified of employee plan participation. The information requirements may vary by provider, product, and benefit plan funding method. For example, the employee enrollment information may be released to the plan provider in one of two formats based on plan funding methods. Such plan funding methods may include non-contributory or 100% employee paid enrollment, contributory or employer/employee paid enrollment, or voluntary (e.g., 100% employee paid) enrollment. For example, employer applications and employee enrollment applications 285, 286 would need to be populated by information available in the application or manually entered. For example, the user (e.g., benefit consultant) may select the forms to be system-generated with the employer and plan information in the application with the system generating the employer/client plan installation report. On corporate authorization for an employer, other installation activities may continue.

Various functionality may be provided by the plan installment and enrollment process 282. For example, an employee plan census listing may be used to enroll/waive eligible plan participants in the new benefit plan. Various edits and modifications to the plan enrollment or the employee plan census listing may be made. Pre-populated plan enrollment forms may be provided with employee information already in the census or demographic data of the system. Further, once the various modifications have been made for employee enrollment, a system-generated, pre-populated employment plan enrollment form may be created. If any information is missing from the enrollment form, a user may provide such outstanding information. Further, such employee plan enrollment form may be edited and viewed to provide accurate information.

Personal health statements may also be a part of the enrollment form. With access being allowed in many cases to the employee, an employee may actually be able to access and accurately complete this portion of an enrollment form.

The system may record employee plan enrollment information for further reference. Such information may be used with ancillary applications such as the export of premium deductions to payroll.

Plan provider installation functionality 288 may then be used, for example, by a benefit provider to install the plan 290. For example, benefit provider plan installation templates may be provided and which are populated with adequate information including, for example, client risk acceptance notification, record employer and employee information, master group policy delivery, initial premium billing statements, and employee plan booklets delivery. The plan installation is provided when the plan benefit provider receives, verifies, and processes the required plan installation and enrollment information. This is provided by a portal available to the benefit provider.

For example, the system may display a listing of plans and a listing of employer/clients. The benefit provider may select a proposed plan to be changed to a plan inforce for a particular employer/client. Upon such a selection, the benefit provider plan installation notification templates may be populated and plan information may be recorded and logged into the system. Summary plan description functionality 292 may then be used to provide various types of information to one or more users, such as the employer/client and employee. For example, a benefit plan description summary may be provided (block 294) as well as claim forms. Further, links to network directories providing additional information to one or more users may also be provided.

Summary plan description 294 is generally a document that employers are required to provide to their employees for their benefit plan. A summary plan description is required when a plan amendment (e.g., plan contract revision or change in provider) affects the employee's benefits. As such, the present invention allows for the summary plan description to be system-generated and may include information such as employer ERISA plan information, a plan summary developed from the benefit plan templates, and other information available through the application, as well as benefit provider generic product text. Such a system generating a summary plan description that is available to the employees may be edited and viewed as allowed by assigned role and task access authorizations.

Further, the application includes plan amendment request functionality 296, as shown in FIG. 2. The plan amendment request functionality is part of a plan amendment cycle that starts with a plan that is inforce. A request for an amendment may be made using the application (block 296), and a plan provider amendment approval process is generally completed in order to produce an amended plan. A plan amendment is generally a documented contract change to the inforce plan contract between an employer/client and the benefit provider during the plan policy year or on the plan policy anniversary date. Generally, an employer is required to sign the plan amendment and is also required to release any of the summary plan description to their employees in the event of a plan amendment.

Plan amendment request functionality 296 is used to generate a request for plan amendment 300. For example, the user, when presented with a list of employer plans, selects a plan and displays the plan template. The user may record the plan changes and name the proposed amended plan request. The system then saves the amended plan. The user selects to release the plan amendment request to the plan provider, as shown by block 300. Thereafter, an amendment response functionality (block 302) is used to respond to the plan amendment request. As such, a plan amendment response 298 is provided in response to the request 296. For example, when the plan amendment request is received by a benefit provider, the benefit provider may view the contents of the request, assess the risk, approve the request to change or deny the request to change, enter the plan rate change (if required), and release their response (block 302) via the application.

One will recognize that this plan amendment cycle may be implemented any number of times until a proper and acceptable amendment is arrived at between the parties involved. Editing, viewing and creating any of such requests and responses may be performed by authorized users.

Plan renewal request functionality 304 generally is used to carry out the renewal of an inforce benefit plan. Generally, the provider provides proposed renewal plan rates and the employer accepts renewal plan rates (or declines and finds a different benefit plan). In other words, plan renewal is the process by which the plan benefit provider prepares the new inforce plan rates for the upcoming policy year. Plan renewal activities may include: plan financial experience analysis, employer demographic analysis, employee demographic analysis, benefit plan utilization analysis, plan design review, plan design change requests, and renewal rate action.

For example, the employer, benefit consultant, and/or benefit provider may initiate the plan renewal process 304. When the employer accepts the provider's proposed renewal rates for the new plan policy year and there are no changes to the inforce plan design, the plan will remain inforce. The user may edit the plan effective date and record the new rates.

Further, if the employer/client does not accept the proposed renewal rates, the benefit consultant and/or the employer/client may negotiate these rates with the benefit plan provider. If both the employer and benefit provider agree to a revised rate and the plan design remains the same, the plan can then remain inforce. The user will edit the plan effective date and record the new rates.

When an employer does not accept the proposed renewal rates and the benefit provider will not negotiate the rates, the employer may agree to change their inforce plan design with the benefit provider. The user may edit the plan design, effective date, and record the rates for the changes to become a new benefit plan. The existing plan would be changed to a historical plan and recorded in history, and the employer/client would need to provide new summary plan description to their employees.

Yet further, the employer/client and/or the benefit broker/consultant may select to conduct a market search for a benefit plan that is inforce. The user would then follow the process described herein for an external marketing of a new plan, and installation and enrollment in the plan, etc.

Such renewal requests and acceptance and/or negotiation may be carried out by one or more iterations of a renewal request and a renewal response functionality 304. For example, a renewal request may be created per the functionality 305 soliciting a response and a renewal response may be released per the functionality of 307. Each of such requests or responses may be implemented by one or more templates such as a plan renewal request template or panel and/or a plan renewal request response template or panel that is used to provide a user interface to the authorized user in making the request or responding thereto. Further, for example, a template for acceptance of a renewal response or request may also be utilized.

Plan provider premium remittance functionality 306 may be used to create a premium remittance statement. For example, a HIPAA compliant premium remittance statement may be derived from the plan rates, the employee/dependent plan enrollment, and the type and/or total amount of benefit. The premium amounts may be adjusted as employee changes are recorded. The statement may reflect such changes. Although, generally, a user will not edit the premium remittance statement, a user may, however, edit the information used to develop the premium remittance statement. Such premium remittance statement may employ a plan premium calculation algorithm 308 operating with plan census summary data 309.

Electronic funds transfer (EFT) remittance functionality 310 may be used to provide for premium payment through a managed, external system interface. In other words, premium payments may be made online. Payment may be accepted by a benefit plan provider, as well as such premium payments being tracked along the payment cycle.

The employer benefit management functionality 230 further provides various tools and templates to perform benefit administration reporting and notification functions. This is in direct contrast to such functions being traditionally outsourced by a benefit consultant.

For example, the functionality 230 provides for various benefit changes and continuance notification functions. Exemplary of such functions is benefit plan age change notification functionality 312 which may be used when an employee/dependent's benefit is reduced due to an age change (for example, group life and group long-term disability). The application may be used to automatically age the census data (e.g., periodically update the census data) and run daily notifications such as a benefit plan age change employee notification 313. The manner in which an employee may be further notified 313 may be defined in a previously-created template such as when the plan is created. The notifications are released in a traceable manner and the system logs such notification activities.

Benefit plan continuance notification functionality 314 may be used when a change in employment status occurs. For example, an employer must notify an employee of their legal and/or plan contract rights when their benefits change due to their employment status change. For example, the application can generate a notification to be released in a traceable manner. Such benefit plan continuance notifications may include, for example, COBRA, conversion, disability, Family Medical Leave Act, lay-off, leave of absence, portability, retirement, state continuance, etc.

Further, for example, other changes may include changes performed via employee handbook functionality 318, which may provide an online employee handbook 319 that can be viewed and edited; an employee benefit statement functionality 320 for creating and allowing an employee to view an employee benefit statement 321; functionality that allows for Section 125/Cafeteria Plan administration (block 322) and provides for benefit financial management 323 of the plan. For example, the Section 125 plan is a tax-qualified plan in which all participants are employees.

The present invention may allow employees to craft their own benefit program on a tax advantage basis. The application functionality, according to the present invention, may be used to provide access to a Section 125 plan and various attributes thereof. For example, an employee may be given access to scan claims into a Section 125 plan for self-service reimbursements from the plan, access retirement account information, receive plan payments 328 such as by EFT 330, etc.

The functionality of the present invention may also provide the ability to generate compliance reports used to meet government requirements. For example, the Federal government requires an employer to meet certain reporting requirements such as employee demographic information or census information reports, ERISA reports such as summary plan description filings, retirement plan filings, welfare plan filings, Section 125/Cafeteria Plan filings, and Section 127/Educational Assistant Plan filings, as well as group life tax reporting.

Not only can employee handbook changes and employee handbook information per functionality 318 be provided to users, the generation of other benefit communication reports may be system-generated using the employer/employee information reported in the plan installation and enrollment processes, as well as the general information gathered for marketing and creating plans. The benefit consultant and/or the employer/client may manually enter information not available in the system. Such reports that may be generated include employee benefit statement reports, employee identification cards, employee handbooks with summary plan descriptions and employer policies and practices, as well as other employee surveys and any other information that may be beneficial to one or more users.

Data mining and reporting functionality of the various client portal management functions 202, as shown in FIG. 2, is shown in further detail by reference number 350. Various types of data mining and reporting may be accomplished according to the present invention and with use of the functionality of the application. Employer benefit management reporting tools and templates may be used to generate unformatted reports (e.g., custom reports where the user selects the fields in the order in which they are to be presented), and formatted reports (e.g., predefined formats that cannot be customized by the user).

For example, the system may display a list of standard report types or allow the user to create a report format. For example, when the user is allowed to customize the format, the system may display the data fields available to include in the report, and the user may select the fields to include and also configure the report as desired. For example, various formatted reports may include employee reports, employee demographic information reports, employee retention/turnover ratio reports, employee termination analysis reports, employer demographic information reports, plan participation analysis reports, etc. Further, other employee benefit management reports may also be generated. For example, such formatted reports may include personal benefit program statements, an employee handbook report, personal health statements, etc. The number of reports and the format thereof is unlimited and therefore the present invention shall provide no further detail other than to indicate that the functionality described according to the present invention may provide data and information that is beneficial to the user in a report form.

The above description with reference to FIG. 2 provides a general overall functionality available to one or more users such as a benefit broker/consultant. The description of portions of such functionality is also applicable to the functionality shown in the flow diagrams of FIGS. 3-6 and, therefore, such functionality may not be described in further detail with reference to such FIGS. 3-6. As such, only portions of the remaining flow diagrams of FIGS. 3-6 shall be described in further detail, with the flow diagrams themselves being a general representation of the functionality available in one exemplary embodiment of an application according to the present invention.

FIG. 3 shows a flow diagram of functionality of a benefit management application, such as application 20 shown generally in FIG. 1A, which may be accessed, for example, by a benefit provider through a benefit provider portal, such as portal 26 as shown in FIG. 1A. A benefit provider may log in (block 400) and either change a password for the user or access one or more benefit provider management functions 402. For example, such benefit provider management functions may include portal image customization to provide a customized portal, benefit provider authorizations to provide one or more users with authorization to access one or more functionalities of the application, benefit provider administration functionality (e.g., application content management functions shown in the diagram as block 410), BC/BC firm administration relating to administrative functionality of multiple benefit broker/consultants, client administration functionality relating to benefit provider access such as that associated with the employer benefit management functionality shown and described with reference to FIG. 2, business/enterprise application administration, data mining and reporting functionality, log notification functionality, translated file format functionality, and archiving data functionality. Portal image customization, provider authorization, data mining and reporting, log notification, translated file format, and archive data functionality have been previously described herein and such functionality shall not be described in any further detail.

Benefit broker/consultant and/or firm administration functionality 406 may provide for various administrative activities. For example, various benefit consultant firms with whom a benefit provider is associated and information regarding such firms may be recorded, as well as one or more various benefit consultants and information related thereto (block 408). For example, such information may be related to benefit provider appointments with the one or more benefit broker/ consultants, as shown by block 409. Further, such information may be related to licensing of such benefit consultants by the benefit provider (blocks 411).

Further, commission accounting of the benefit consultant firms, and employees thereof, as they relate to various employers/clients which have plans with the benefit provider user, may also be accommodated (block 412). Benefit provider resource center (e.g., including enrollment forms, claim forms, etc.) may also be a part of such functionality, as shown by block 414. Likewise, various calendaring functions may be provided via the contact management information functionality 416.

One will recognize that any administrative functions of the benefit provider relating to the benefit chain, such as activities where both the benefit provider and the benefit consultant may need access to similar information, may be implemented according to the present invention. The functionality described only in block 406 is not to be taken as limiting the types of application functionality that may be implemented. Further, various ancillary application functionality, such as that shown by block 418, may also be accessible by the benefit provider. For example, such application interfaces may include contact management, CRM, sales management, licensing, commission accounting, plan premium accounting, and plan enrollment/maintenance.

The application content management functionality 410 generally pertains to the provision of various types of information useable by the application 20 to perform one or more various functions. For example, benefit providers will have various product templates 422 which need to be presentable to a benefit broker/consultant along with product matrix information such as that used for underwriting requirements, etc., as shown by block 424.

Further, rate calculation engines such those including algorithms for determining premiums is functionality that needs to be populated and updated by the benefit provider. For example, such a rate calculation engine may need updated rate tables, underwriting factors, etc.

Yet further, summary plan description text is also required such that employers/clients who adopt a plan provided by the benefit provider can provide such information to its employees. Such summary plan description text functionality is shown as block 430.

Further, the benefit provider may provide a resource center 440 that includes one or more various types of information and forms/templates to be used in, for example, enrollment and installation of a plan for a particular employer/client, etc. The provider resource center 440 may include various enrollment forms, claim forms, network directories, company profile information, product information, contact management information, or any other benefit provider information that may be beneficial in marketing their products. The provider research center functionality provides for the creation, viewing, editing, and deleting of one or more portions thereof, as shown by block 441. It will be recognized that each flow diagram herein includes sub-blocks, such sub-block 441, that is used to show an exemplary type of authority that a user may have with respect to the functionality with which it is associated. It will be recognized that such authority is exemplary only and may or may not be the actually activities allowed by the users.

Yet further, the application contact management functionality 410 may include sales force management functionality 450. Such sales force management functionality may include information about the various sales offices, the name and number of sales representatives, the various benefit consultant firms with which the benefit provider works, and/or the various benefit consultants with whom the benefit provider is associated. This information is then generally available to all those needing such sales management information.

The client administration functionality 460 generally relates to the benefit provider's interface with a benefit broker/consultant using, for example, one or more functions provided in the employer benefit management functionality 230 shown in and described with reference to FIG. 2. For example, various types of information can be viewed using the application 20 including employer benefit management data, employer information, employee information, and requests for proposal documents, as shown by functionality 462 in FIG. 3. With such information, a benefit provider has the information (e.g., employer information, census information, employee health statements, etc.) to generate a RFP response (block 464).

Further, other actions, which are typically performed if the benefit provider has acceptance of the RFP response by the employer/client, can then be carried out. Such functionality is generally shown by functionality 466 in FIG. 3. For example, the benefit provider must engage in the plan enrollment and installation process, plan administration, plan maintenance, plan premium payments, plan amendment request and response process, plan renewal and response process, plan financial experience, and any plan claims payment process (e.g., such as an EFT payment process). Access to such application functionality by the benefit provider is easily understandable from the description provided with reference to the employer benefit management functionality 230 described with reference to FIG. 2.

FIG. 4 shows a flow diagram for the functionality in one embodiment of the application available to employees who have been properly authorized by an employer to access such functionality, as shown by block 500. Also, as shown in block 500, it will be recognized that the employee portal may be customized or branded, such as, for example, by the employer. Such an employee portal may be implemented, for example, as a child portal of a satellite site in an application architecture 12, as generally shown in FIG. 1A.

An employee, e.g., through the child portal, may have access to various employee portal functionality 502 upon login 501. For example, such employee portal functionality 502 may include access to benefit statements, benefit notifications, an e-reference library, employee benefit handbooks or employer handbooks for policies and procedures, log notification functionality, and data mining and reporting functionality. Such functionality should be readily understandable from other description herein, and further detail with regard to such functionality shall not be provided.

Further, employee portal functionality 502 may include plan administration functionality 504. Such plan administration functionality may allow an employee to view one or more benefit plans and options, proceed with enrollment and/or maintenance with regard to such plans, view summary plan descriptions of the benefit plans, and/or view other information with regard to the benefit plans from a benefit provider resource center.

As previously described herein, the benefit provider resource center may provide plan enrollment forms, plan claim forms, and benefit plan network directory assistance, as shown generally by block 506, such that an employee may make an informed benefit forms selection and be able to provide in a self-service manner completed enrollment forms for enrolling in a benefit plan 508.

Personal benefit spending account functionality 510 may allow an employee to perform certain functions, such as self-service claim entry/claim reimbursement 512.

Further, various types of data 520 may be created, viewed, or edited by an employee depending upon its confidential status and employee authorization. For example, health statements may be created, viewed, and edited by the employee to create a personal health statement, as shown by block 522, along with personal manager life events and personal health planner information 524.

In addition to the functionality available to a benefit consultant or a benefit consultant firm, as described with reference to FIG. 2, FIG. 5 shows additional agency/enterprise management functionality that may also be accessible for use by a benefit broker/consultant (e.g., a benefit broker/consultant or a benefit broker/consultant firm). Upon login (block 550), a benefit broker/consultant may access certain management functionality 560 through a benefit broker/consultant portal, such as portal 24 shown in FIG. 1A. The management functionality 560 may include portal image customization, ancillary business/enterprise application functionality, data mining and reporting functionality, log notification functionality, translated file format functionality, and archive data functionality, in a manner similar to that previously described herein and which shall not be provided in any further detail.

The business broker/consultant portal management functionality 560 may also include benefit consultant administration functions 562, employer/client administration 566, and benefit provider administration functionality 568. With respect to the benefit provider administration functionality 568, a benefit broker/consultant may, for example, be able to view various benefit provider information. For example, such information may include benefit provider administration information such as information regarding providers with whom the benefit consultant firm is associated, various benefit provider resource centers having information from the benefit providers, and methods for providing provider commission accounting, as shown in block 570.

Further, for example, certain calculations with regard to commissions may be viewable, as shown in block 572. Plan commissions payable 573 to the benefit consultant firm may be calculated and also payment may be made by EFT (block 574).

Yet further, the benefit consultant may be able to view and also may have authority to authorize particular benefit providers to have access to certain functionality (block 575).

Employer/client administration functionality 566 may provide a way for the benefit consultant to create employers/clients and perform client billing thereto as well as authorizing employers to be able to access certain functionality of the overall application, as shown generally by block 580. For example, client invoices may be generated to bill employers/clients and payments may be received by EFT remittance.

Firm administration functionality 564 may provide the benefit consultant firm with various functionality and information. For example, the firm administration functionality may be used to control who has authorization to use the application (block 582), may provide appointment scheduling with benefit providers (block 584), and/or may include contact management information functionality for providing access to one or more benefit providers, one or more employers, one or more medical providers, and/or one or more business vendors (block 586). Further, firm administration functionality may include a reference library for access by the benefit consultants of the firm and the firm profile thereof, as shown in block 588.

Yet further, the benefit consultant firm may have certain preferred plan templates and/or client proposal formats which it may desire its business consultants to use and provide access thereto, as shown by numeral 590. In addition, the firm may have other certain proprietary marketing information such as firm profile information and firm marketing information, which may all be created, viewed, edited, or deleted by the firm administrator, as shown generally in block 592.

For example, a benefit consultant may choose to use empty templates to develop proprietary plan templates to store in their plan reference library for use when creating a plan. Such functionality is provided by, at least in part, firm preferred plan template functionality 590. Likewise, proprietary client proposal formats may be provided by such template functionality 590.

Yet further, the firm administration functionality 564 may include functions for performing commission accounting and/or allowing such commission accounting to be viewed by the benefit consultants. Further, sales management data relating to benefit providers, employers, benefit consultants, and sales offices may be available for use in sales management activity. Such commission accounting and sales management are shown generally in respective blocks 594, 596.

Firm administration functionality 564 may also be used for keeping track of licensure. For example, a user may select to record state insurance firm license information, including a scanned image of the firm license, as shown by block 583. Further, a system generating a notification to be released to the firm license holder within a specified number of days prior to the expiration of the state insurance license may be provided.

Further, a firm is required to be licensed by a benefit provider in order to represent the benefit provider and to receive commissions therefrom. As such, provider appointments functionality 584 may be used to request appointments, receive responses to such requests, and maintain such appointment or licensure by a benefit provider.

Further, the portal management functionality 560 provides benefit consultant administration functionality 562 that is designed to offer the benefit broker/consultant firm an internal agency/enterprise management system for their office that focuses on their group insurance clients with integration and/or interface to other existing business applications. The benefit consultant administration functionality includes the creation of one or more benefit consultant records, as shown by block 598. For example, the system may display a template to enter information regarding the one or more benefit consultants.

The benefit consultant and/or firm may create a reference library generally represented by block 600 for use in organizing and cataloging information, forms, templates, and records to manage their business operation and their client base. These records may be created, edited, and viewed on a regular basis and include, for example, professional profiles, state insurance license records, continuing education records, provider appointment records, contact management information, preferred plan templates, preferred client proposal formats, marketing and professional promotional materials, and business insurance and bond information such as auto, employment practices, fidelity bond, fiduciary liability, property, and workers' compensation.

For example, a benefit consultant may choose to create a professional profile to be used in a client presentation. The profile may include business professional information, educational background and training, industry/product specialization, and accreditations to promote their image. The application provides a customizable benefit consultant template that may be used to present such information.

Further, a user may provide state insurance license records by selecting to record state insurance license information including a scanned image of the license. Further, renewal dates and reminder messages may be added in calendaring functions so as to be able to maintain proper licensure.

Further, a benefit consultant may use the application to create continuing education requirement notifications and to update information and records regarding continuing education requirements and activities.

Further, a benefit consultant is required to be licensed (e.g., appointed and/or contracted) by a benefit provider in order to represent the provider and to receive 30 commissions therefrom. As such, the functionality of block 600 may be used to create a provider appointment request by the benefit consultant. The provider may then provide an appointment response with maintenance of such appointments throughout the benefit consultant's representation of the benefit provider.

The data mining and report functionality of the management functionality 560 may provide various formatted reports such as sales force management reports, commission accounting reports, and benefit provider business management information reports. Further, for example, and in no manner limited thereto, such formatted reports may include requests for proposal tracking, new business reports, renewal business reports, financial profit and loss reports, etc.

FIG. 6 shows a flow diagram of the functionality available to an application administrator through, for example, an administrative portal 22, as shown generally in FIG. 1A. Generally, the application administrator will manage or maintain the information content, including the following templates or panels, for use in interfacing with one or more users: employer information templates, employee demographic information templates, master product templates, standard plan templates, request for proposal templates, rate calculation engine standard plan templates, client proposal master templates, employer plan installation and provider reports, employer plan enrollment and provider reports, benefit provider plan installation forms and reports, summary plan description master templates, premium remittance statement templates, benefit plan age change notification templates, benefit communication forms and report templates, benefit plan continuation and/or notification forms and reports, compliance processing and reports, Section 125 plan administration forms and reports, formatted data reports, e-reference/resource library links, constant tables, professional profile forms and reports, licensing forms and reports, continuing education forms and reports, provider appointment forms and reports, contact management templates, internalization/content translator templates, import/export file formats, and portal image branding templates. In other words, an application administrator user may choose to select and edit, delete, or create one or more report formats or templates for any use as described herein to provide functionality as described herein.

Upon login (block 640), the application administrator may have access to various portal management functionality 642. Such portal management functionality 642 includes customized portal image functionality, log notification, ancillary applications, e-reference library functionality, data mining and reporting, translated file formats, and archive data functionality, such as previously described herein and which shall not be provided in any further detail.

Further, portal management functionality 642 includes constant table functionality 644 for use in maintaining tables of the application. Further, the e-reference library also requires maintenance. The application administrator may further have access to sales commission functionality 646 such that sales commission templates may be maintained. Further, HIPAA compliance functionality such that a HIPAA application compliance program can be implemented and carried out, is shown generally by block 648. Sales demonstration functionality 650 is also part of the portal management functionality 642 to provide a way for the application administrator to sell or license this product to one or more users, such as, for example, benefit broker/consultants, and/or, to employers.

Provider administration functionality 652 may be used by the application administrator to create benefit providers and information related thereto, and further to allow for the creation of a provider resource center for such benefit providers. The administrator provides proper user authorization thereto for populating templates or panels related to such benefit provider information, as shown generally by block 654.

Further, portal management 642 includes client billing and receivables functionality to generate client invoices and receive EFT remittances, as shown generally by block 655.

User administration functionality provides the application administrator with the ability to create users and user authorizations to allow others access to the application functionality. For example, the application administrator may control user authorization for employees thereof, benefit consultants, employers, and benefit providers. The benefit consultant may provide user authorization to benefit consultant employees, employers, and employees of such employers. Further, for example, the employer/client may provide user authorization for employees thereof and, likewise, a benefit provider may provide benefit provider employees with user access.

In one general authorization configuration, the application contains a master list of tasks. Each user type will have an associated task list. An authorized user will be able to custom assign tasks to a user within the hierarchy. One will recognize that user access to the application may be controlled in one or more other manners. For example, as described elsewhere herein, user access to certain roles, tasks, and data may all be controlled by different security requirements. For example, access to the application via satellite sites and/or child portals may provide certain user authorization techniques.

Further, the application administrator may maintain all product templates, including the master template, by which benefit consultants may create preferred templates of plan designs. Such benefit product template maintenance is shown by block 660. Summary plan description (SPD) plan templates may also be provided through the portal management functionality 642, as shown by block 662, as well as employee handbook templates, as shown by block 666.

Further, as shown by blocks 668 and 670, and those associated with numeral 672, client authorization to allow access to the application functionality is generally controlled by the application administrator. For example, as shown in block 672, benefit consultant firms may be recorded and authorized, employers may be recorded and authorized, etc.

The architecture 12 for implementing one or more portions of the functionality of method 10 shown in FIG. 1 may utilize a number of different technologies (e.g., hardware and software) and may include various architectural configurations. For example, one or more different multi-tiered application server architectures can be used to implement the e-business functionality of the present invention involving a large numbers of users.

Figure 8:
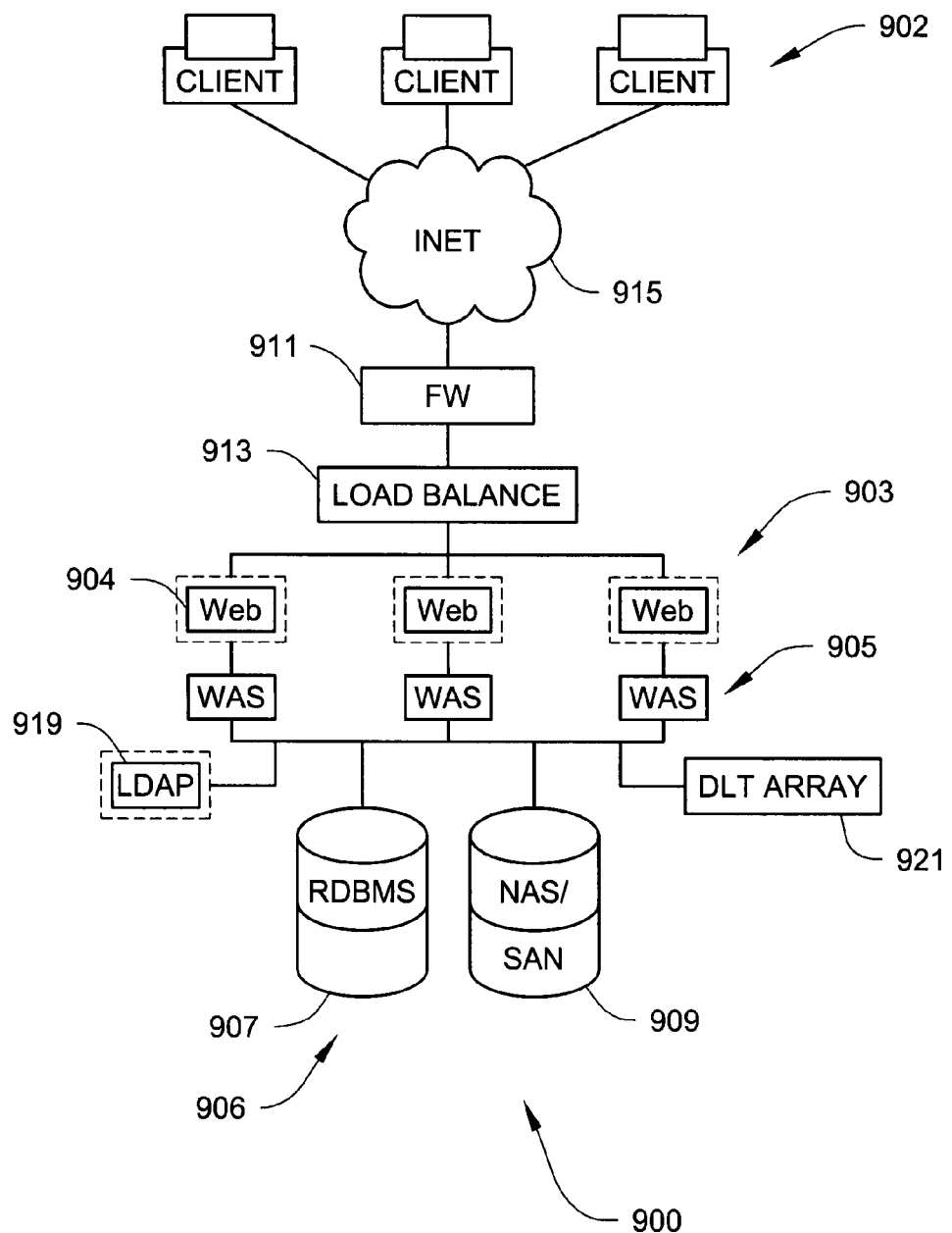
FIG. 8 is a high level diagram of one architectural structure that may be used to implement the present invention.

For example, such a multi-tiered architecture 900 for an application service provider (ASP) is shown in FIG. 8 as a multi-tier configuration, including three layers 902, 904, 906. The client or presentation tier 902 may be hardware/software configuration that allows a user to interface with the middle tier 904. For example, the client tier 902 may be a browser which executes the application's user interface with which the user directly interacts. The middle or application tier 904 is preferably a layer in which business logic and program intelligence chiefly exists. For example, in a web-based environment, the middle tier 904 can be thought of as having two distinct layers of its own—one in which web servers 903 reside, and one in which application servers 905 reside. Further, for example, where simple HTML web pages are the primary content, the web serving layer of the middle tier 904 is often considered to be part of the presentation tier. The application server 905 provides the environment in which components, implementing portions of the business logic, reside. The data tier 906 is the layer where application data is saved for users, typically in a relational database architecture (e.g., a relational database architecture including a relational database management system (RDBMS) 907 and data storage 909, such as network attached storage (NAS) and/or a storage area network (SAN)). Generally, communication occurs between tiers only, e.g., the presentation tier 902 interacts strictly with the middle tier 904, and the middle tier interacts strictly with the data tier 906.

Generally, as also shown in FIG. 8, a firewall 911 provides for certain security measures, and also load balancing or router hardware/software 913 may be used to distribute information across the web servers 903. In addition, the tiered network architecture includes managed switches (not shown) as would be known by one skilled in the art. Yet further, a directory services structure 919 is also provided as shown by the exemplary lightweight directory access protocol (LDAP) and also backup functionality 921 as shown by the exemplary digital linear tape (DLT) array. It will be recognized that at least the dashed line elements of FIG. 8 are generally optional elements in at least one embodiment of the multi-tiered configuration 900.

Such an architecture 900 may be beneficial to an ASP in that the client tier 902 may be the end-user's browser which exists outside of the ASP, while the middle tier 904 and data tier 906 reside at the ASP. In software, the communication traffic between the client tier 902 and middle tier 904 is relatively light compared to that between the middle tier 904 and data tier 906 since the client tier 902 is mainly performing interactions with the user, which doesn't require much data, while the middle tier 904 is executing business logic, which does. The Internet 915 sits between the client tier 902 and middle tier 904, which services this lighter traffic, while the ASP's high-performance internal network services the heavier traffic on the back-end. Note also that the browser-based client tier 902 does not require administration by the ASP, while the other tiers do.

Various other generalized hardware/software architectures could be used. For example, a two-tier, flat client or client server architecture could be used. In this model of computing, there are two tiers—a client tier and a server tier. The client tier combines the functions of the presentation and middle tiers from the architecture described above. The data tier remains the same.

Further, a thin client computing model may be used. For example, in this model of computing, a two-tiered application is hosted at the ASP, and users interact with a terminal tier. Products such as Microsoft Terminal Server or Citrix Win-Frame/MetaFrame provide this service for existing client server applications.

Further, other computing architectures may include three-tier computing without an explicit application server, wherein this model of computing is identical to the application server architecture except that the middle tier doesn't have two sublayers, there is no application server, and the middle tier code executes in the web server itself.

Further, message-orientated middle wear solutions such as MQ-Series, TIBCO, etc., may be used. Such models are characterized by a common information bus that serves as a shared medium for exchanging messages between applications that are connected to the bus.

In one embodiment, the present invention uses a portal architecture that brings the robustness of Java technology and object-oriented technology to web applications, but with an easy-to-use administration tool for the most common kinds of web maintenance: user security, data management, content management, and marketing campaigns. Generally, the portal architecture follows the general design model 1000 shown in FIG. 9. The architecture preferred for the present invention is a platform that is specifically designed and developed to provide managed web application support without the cost or complexity of traditional large-scale J2EE applications. By building robust business objects 1050 and presentation panels 1040 for interacting with them; a persistence layer 1005 that includes an XML-based object-relational mapping and transaction layer; and application programming interfaces (APIs) for security, workflow, and messaging, the portal architecture, according to at least one embodiment of the present invention, allows for complex, customized application functionality at a small fraction of the cost and complexity of traditional distributed applications. In other words, the functionality described herein for application 20 can be implemented using such an architecture. As scalability needs grow, or uptime requirements become more demanding, the architecture supports clustering and load balancing of application servers without the need for expensive J2EE application servers. The architecture (e.g., one embodiment of the multi-tiered architecture shown generally in FIG. 8) requires only a Java Servlet Container, such as Apache's Jserv or Tomcat, running on the application servers and a single file server and relational database server to share files, images, and data among the multiple application servers. A web server (such as Apache or Microsoft Internet Information Server) may also be used, although such web servers are optional.

Figure 9:
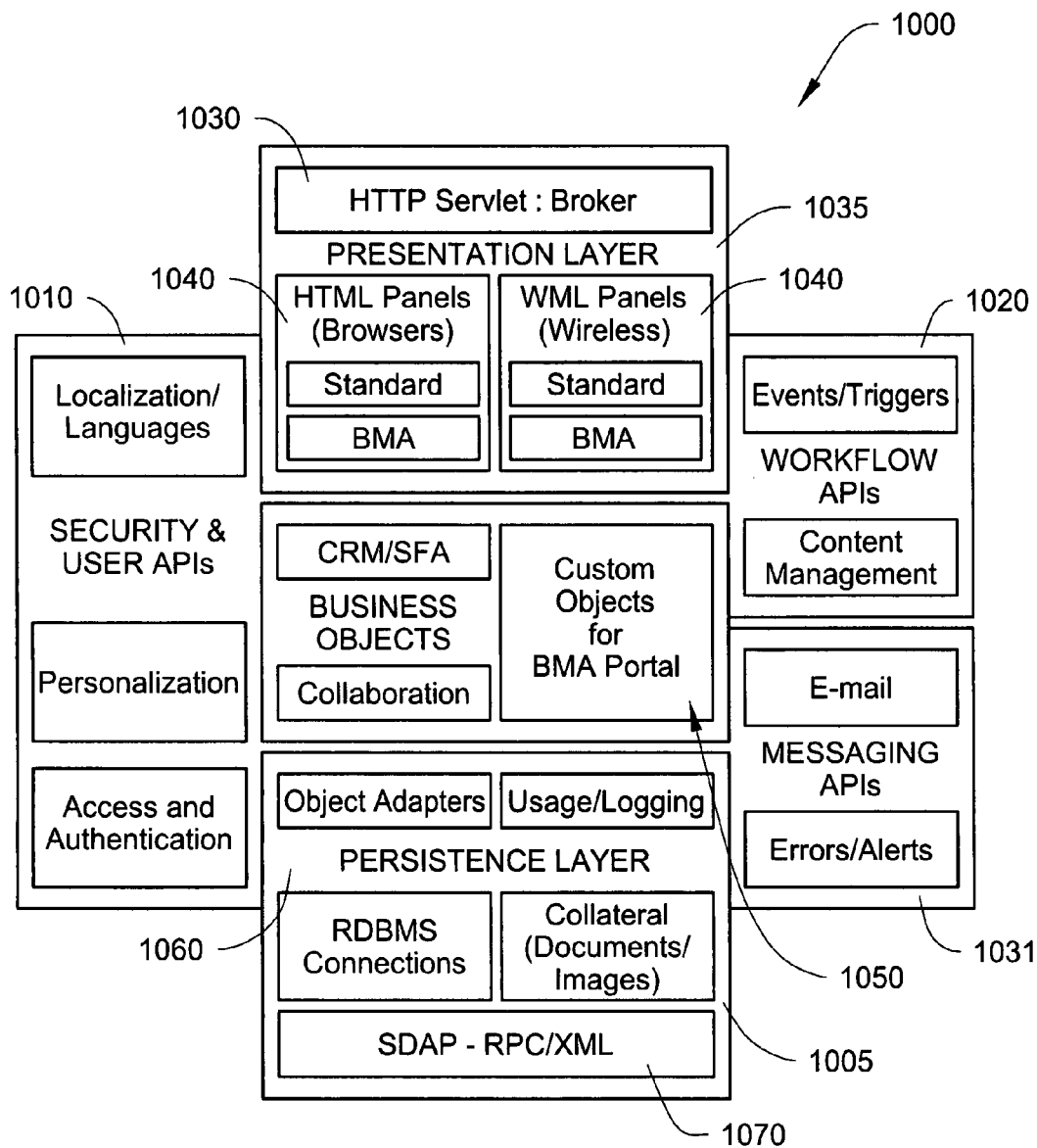
FIG. 9 is one block diagram illustrating a general model used to implement one or more portions of the functionality shown in FIG. 1A, according to the present invention.

Further with reference to site architecture and management in the model 1000 shown FIG. 9, the application portal handles all HTTP requests with a framework broker servlet 1030. This servlet 1030 is responsible for marshalling requests, parsing forms or multi-part attachments and invoking the site (e.g., persistence layer 1005 and presentation layer 1035) and page objects associated with presentation panels 1040 (e.g., user interface portions providing a user with plan design templates for building plan designs, templates for summary plan descriptions, templates for recording information regarding employers, employees, etc., as well as any other templates for use in performing functionality as described herein). The site and page objects are responsible for managing user sessions and authentication, personalization settings, database connections, and other site-wide parameters and events. The presentation site object is responsible for rendering the HTML (or WML) responses from the business objects, whose interfaces are represented by presentation panels.

At least in one embodiment of the present invention, the presentation panels are at least one core portion of the application. The presentation panels 1040 are composed of Element and Group Objects, plus Business Objects 1050, to create reusable, configurable application components that can be aggregated into web applications. The Element Object Set represents the HTML and WML Document Object Models as Java Objects, as well as Java Object representations of Cascading Style Sheets, JavaScript, and GIF and JPG Images. Group Objects represent common aggregations of elements such as tables and lists. Panel functionality is written using Java, with a combination of custom functionality and interfaces to the Security and User APIs 1010, business type Workflow APIs 1020, Messaging APIs 1031 for use in managing messaging functions, and persistence layer 1005.

In addition to the Java Object representations, the application contains a wrapper panel for raw HTML mark-up, allowing administration users the flexibility to create their own content without having to rely on developers to create Panel representations. These wrapper panels can be stand-alone, serialized, or hierarchical. Serialized and hierarchical HTML panels must have companion navigation panels; the former organizing the presentation by date, and the latter into hierarchical navigation structures.

All elements of a Panel have an ID and RDBMS or File System data store as represented generally by numeral 1060 in the persistence layer 1005. This provides a way for all text, images (including text on images), and raw HTML to be edited (e.g., with complete workflow rules for approval and publishing) using an application portal administration tool. This architecture also allows for multi-language site creation using a single site instance and single graphics set.

Figure 10:
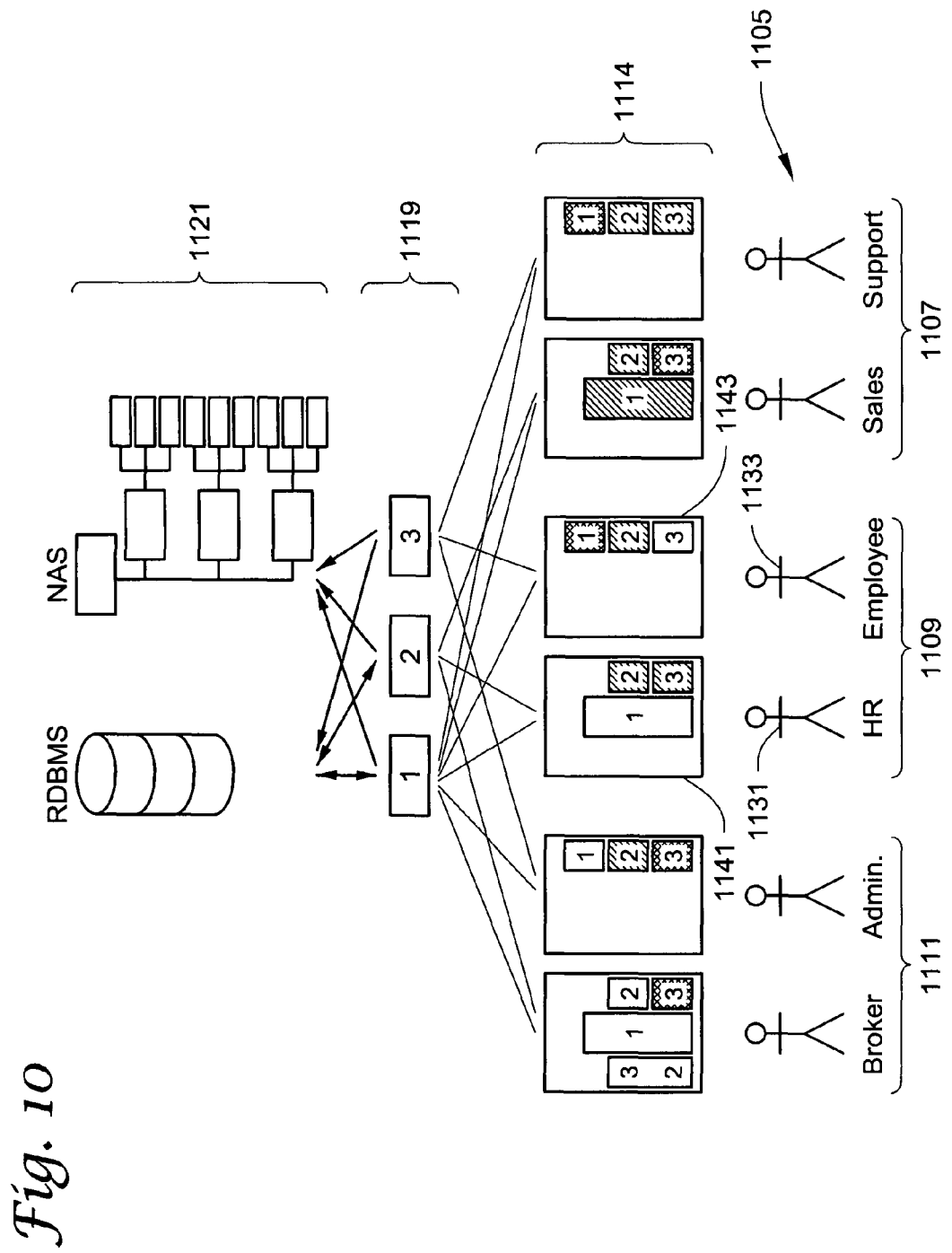
FIG. 10 is a block diagram showing in more detail a role- and portal-based view of a portion of the model shown generally in FIG. 9.

One of the key features of web applications is that many different types of people, both within and outside an organization, can access the organization's data, as well as participate in business processes that occur. However, that also means that various services, ranging from personalization to authentication to security, for private or confidential data or internal business processes, need to be provided. For example, as shown in FIG. 10, such services are provided for various users 1105 of the present system according to the present invention. Such users 1105 may include benefit provider users 1107 (e.g., sales and support staff), employer/client users 1109 (e.g., human resource and employees thereof), and/or benefit broker/consultant 1111 (e.g., a broker or administrator thereof).

As shown in FIG. 10, user portals 1114 are provided for such users 1105 and services such as personalization, authentication, and security are provided depending on the user. For example, different users 1105 as generally represented by the different blocks in the user portals 1114 will be allowed access to different portions of the application functionality shown generally by the presentation panel/business objects portion 1119 of FIG. 10. Further, likewise, access to data/documents (e.g., employee benefit information provided via the RDBMS and NAS through or by way of a business object or presentation panel) may also be controlled.

For example, with respect to authentication and security, the application 20 may issue a globally-unique ID (GUID) to each user 1105 at login. The Site and Panel objects then use this parameterized GUID to look-up the role, relations, and personalization preferences for this user. The GUID may be generated using several different pseudo-random functions at each login, and expires according to a configurable time-out.

The panel developers use the concepts of role, context, and relation when developing the behavior of panels and business objects. Roles allow various levels of presentation of HTML elements, data access, and edit-control access to be encapsulated in a single component. Context and relations work with roles to allow promotion or demotion of users, given their relation to other data or users in a given context. For instance, if there are context and relation rules in a panel, a benefit broker/consultant may only see her own client data. These rules are written into panels using the role, context, and relation APIs (e.g., security and user APIs 1010 shown in FIG. 9).

All panels, as well as the Site objects, take advantage of the personalization APIs. These allow the personalization of everything from the state of a Group object (e.g., collapsible panel, sorted list) to the language in which a site is displayed.

In other words, FIG. 10 shows how users 1105 would see the hardware/software system through role-based satellite sites (e.g., user portals available for users to access one or more portions of the application functionality based on the role of the user). For example, with respect to users at an employer 1109, an HR person 1131 and an employee 1133 will have different roles in the benefit supply chain. As such, the satellite site 1141 is defined for an HR person 1131 differently than for the employee 1133 that may have access through satellite site 1143 (e.g., a child portal as described herein). For example, a user may have different rights (e.g., view only, read/write, access denied parameters assigned thereto). As described herein, certain users are able to create such authorizations for others (e.g., a benefit broker/consultant 1111 for an employer/client 1109; an employer/client 1109 for an employee 1133 thereof).

Figure 12:
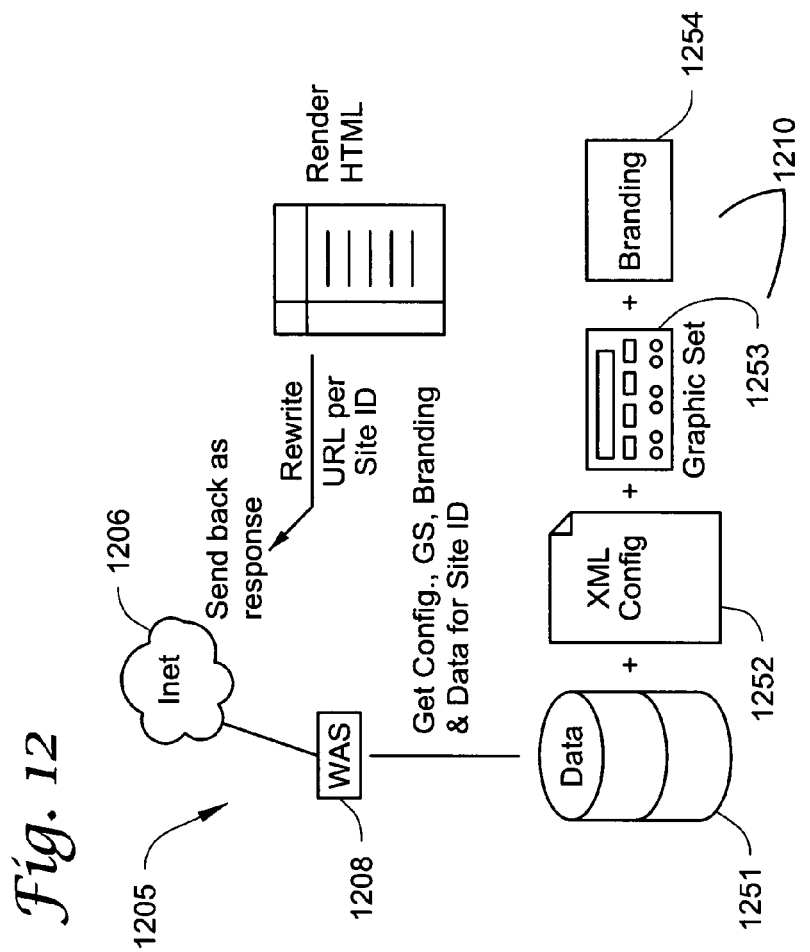
FIG. 12 is a flow diagram showing how satellite sites or portals are built from the models shown generally in FIGS. 9 and 11.

One embodiment of a satellite site 1205, or management thereof, is shown in FIG. 12. The satellite site 1205 is a separately-configurable extension of application portal instances. For example, if a broker were to implement the application portal at the URL (bma.mybroker.com), they can extend the user of that portal to their customers by simply assigning them a role in authentication (user/password) within the broker's portal. In other words, a parent site can control the base roles, permissions, panel configurations, etc. for a satellite site. However, the satellite site administrator can only further restrict such roles, permissions, etc. Such roles, permissions, etc. are preferably not expandable.

Further, satellite sites preferably support creation of one or more child portals, e.g., a portal at employer.mybroker.com, containing all the data at mybroker.com that is related to the customer, extending the mybroker.com implementation and allowing the employer.mybroker.com site administrator to customize the views, security and look-and-feel of their satellite site. With the exception of HIPAA-protected data, for example, in one embodiment, the mybroker.com users have access to all data in the satellite sites of their portal, allowing the benefit broker to configure and use the application portal as their business requires, and their related benefit providers and employer/clients to configure and use it as they require. With the application graphic sets, all presentation panels are composed of configurable graphic icons and labels. Site administrators can configure almost every visual element in their site without the aid of a webmaster or graphic designer.

Figure 11:
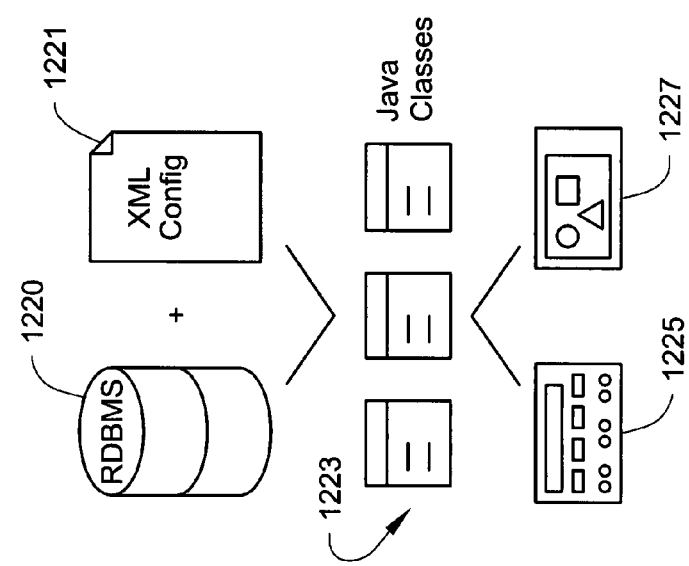
FIG. 11 is a block diagram showing the constituent parts of a site or portal built from the model shown generally in FIG. 9.

As shown in FIG. 11, satellite site components include a relational database (rdbms) store 1220, XML configuration files 1221, Java classes 1223 representing the various business and presentation objects for the application 20 panels, a collection of one or more graphic sets 1225, and other collateral material such as document templates or branding images 1227. Typically, the Java classes 1223 are written in such a manner as (in addition to their interfaces to the various APIs described in FIG. 9) their variable presentation and security properties and behaviors can be stored in the relational database by a siteID, which can be parsed from the URL passed during an HTTP request. Preferably, a site administrator would specify these properties, as well as choose a look-and-feel defined by one of the graphics sets 1225, via web-based site administration tools. For example, corporate branding elements (e.g., typically images depicting the corporate logo) may also be stored with the other collateral 1227, with metadata about the use and location of these images being stored in the relational database 1220 by siteID.

As shown in FIG. 12, a user accessing the satellite site 1205 using the Internet 1206 would be provided with a customized site upon login as the web server application 1208 is used to retrieve a configuration for the user, branding to be used for the user, and/or other information as the user is allowed to access. In other words, responses including one or more various types of information (e.g., branded interface, templates, information, etc.) 1210 can be provided back to the user based on a combination of the ID of the user, in the case of personalization elements (e.g., role-based security and panel presentation, language, data sorting preferences, user-interface control states, and/or data previously entered by that user) and the siteID, which determines which satellite site's database instance 1251 and configuration of role-based security and other configurable elements 1252, graphic sets 1253, collateral directories 1254, that can be accessed. Once this data is gathered by the business objects 1050 (as shown in FIG. 9), the presentation layer objects 1040 render and return an HTML page specific to that user for that role for that satellite site. In this way, a single set of deployed Java objects on the web application server 905, combined with a single rdbms server 907 and file system located on a network attached storage or storage area network 909 can generate HTML pages representing an unlimited number of sites from a single infrastructure deployment.

In addition, the configuration of a satellite as represented by the data stored in the relational database 1251 and configuration files 1252 is hierarchical, so that a child satellite site could inherit, typically, role-based security and presentation configuration which they could further restrict, but which, as specified by a site administrator according to legal or business rules, the child sites could not override or expand. Preferably, the non-HIPAA regulated or other unrestricted configurations could be made by the child site administrator without restriction by the configuration or other parameters set by the parent site administrator.

The application provides two separate role-based security mechanisms; presentation and data. The presentation components of the application are made up of individually configurable panels that can have their three-state view property (hide|view|edit) configured by user or role. This allows site administrators tremendous control over which kinds of users may perform which tasks. In addition, each role (e.g., overrideable by user) has a configurable data security rule (userid=loginuserid, for example, or userlocationid=recordlocationid) for each panel.

In addition to the role-based presentation and data security, the application portal contains many security-oriented features, such as use of Secure Socket Layers plus encrypted URLs to prevent packet filtering or data-spoofing, separate back-end database instances for each broker client, persistence layer change-logging and user-logging and simulated delete of data to prevent user tampering of records.

Further, preferably, the application 20 has extensive object and data model support for tracking the usage and other behaviors of both logged in and anonymous users.

A core feature of the application's persistence layer 1005 is preferably the use of an XML-based Object-Relational Mapping and Transaction engine. Such an engine takes as its input an XML document that conforms to our data model DTD (an XML DTD designed to encapsulate OR Mapping and Application Metadata information such as RDBMS type and Site parameters), and then generates Java Adapter classes. This allows developers to use simple GET and SET methods, with optional transaction and security parameters, to extract from and persist web application data to a relational data store without writing tedious SQL queries or managing database connections. The datamodel.xml document can also used by various import, export, and reporting wizards to generate error-free queries without using SQL.

The persistence layer 1005 also contains a SOAP/XML engine 1070 with methods for import, export, and synchronization of data according to predefined or custom queries, with support for authentication and Secure Socket Layers (SSL). There is also an HTTP-Servlet Query broker interface to import, export, and synchronization APIs for working with third-party HTML forms or for extracting data from third-party web pages.

Finally, there are command-line utilities for managing indexes, schema changes, and dump/load of databases. Various database structures may be used according to the present invention, such as, for example, one or more of the following relational databases: MS SQL Server 7 and SQL Server 2000, Access 97 and Access 2000, MySQL 3.23, and Oracle 8i and 9i.

The application also preferably includes an applet-based report query wizard and web-based report center. Reports can be returned as either panels with hyperlinks to core object panels, or as delimited text-files for tasks such as Microsoft Word mail-merge or Microsoft Excel spreadsheet analysis. All reports can be secured for role-based access.

For more complex reports, the application 20 may include extensive reporting, charting, and graphing API support for using the graphics APIs to display data as sophisticated columns/tables, pie, bar, and line charts—complete with automatically-generated legends and labels.

Small to medium businesses should not take risks with scalability and performance, not any more than large enterprises. As such, the application was architected (e.g., see, for example, FIG. 9) to support the most scalability and performance possible with the least expenditure, particularly in supporting software. With strong Linux and Microsoft Windows 2000 support and portable Java architecture, load-balancing and fail-over are almost trivial from a software cost standpoint.

In other words, as described above, the application 20 is a client-driven, web services business application with server-based integration. It includes functionality for performing transactions, business processes and embedded analytics as described herein. The following approach in constructing the application and supporting infrastructure was taken. The application generally has common data center hardware, an Open Source OS, RDBMS and Application Server Stack (e.g., layers), along with a Java Portal Engine.

Preferably, the data center uses pre-defined "pods" (e.g., data center 906 as shown in FIG. 8) that includes off-the-shelf hardware from vendors such as APC, Cisco, Dell, IBM and open source software such as the Linux OS, MySQL database and Apache Tomcat application server. For example, rack-mounted pods including of switches, load balancer, 2-4 web/application servers, firewall server, secure services server, relational database server and network attached storage array, may be used to configure the system (e.g., the system architecture 900 of FIG. 8). This infrastructure allows for scalability of the data center rapidly using off-the-shelf hardware and open source software simply by adding new pods to the racks.

The core of the application 20 is preferably the Java Enterprise Application Portal (EAP) as described herein with reference to the model 1000 of FIG. 9. This is a servlet-brokered framework and supporting API's for delivering rapidly-developed, highly-configurable and parallel-scaled Web, Wireless and Web Services applications. This framework is inherently parallel, with the single relational database instance the only limit to scalability. For example, a single dual CPU server can serve a pod of four web/application servers running the application. The application includes support for satellite sites, configurable graphic sets, role-based presentation and data security; and in addition, architecture support and API support for HIPAA compliance, as well as other functionality described herein.

The application 20, at least in one embodiment, is deployed using a web-hosted internet platform that functions as an intranet for the benefit broker/consultant (and/or its employees), as well as an extranet for their employer/clients and benefit providers. This networked functionality does not require an on-site server and the related support expenses. For example, an application end-user may just require a standard dialup (56K) connection with better performance requiring a 256K connection (DSL or Cable Modem). Standard computer system setup is contemplated according to the present invention.

All references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. A method for use in providing employee benefit management services, the method comprising:
    providing a hardware/software architecture comprising at least one computer system;
    providing an application comprising one or more programs executable by the hardware/software architecture to perform one or more employee benefit functions using an associated relational database, wherein the associated relational database stores employee benefits management plan data, wherein the employee benefits management plan data comprises:
        at least one benefit plan derived from at least one benefit plan design creation template, wherein the at least one benefit plan design creation template comprises at least a plurality of selectable benefit plan details quotable by more than one benefit provider of a plurality of benefit providers, and further wherein the application comprises a plurality of presentation panels to provide information to a user, wherein the presentation panels provide at least one of user perceivable graphical elements and user interaction graphical elements, and further wherein the at least one benefit plan design creation template is configured as at least one presentation panel; and
        employee demographic information comprising personal health statement information derived from at least one employee demographic information template, wherein the at least one employee demographic information template comprises at least a plurality of selectable details to be used by more than one benefit provider of a plurality of benefit providers, and further wherein the at least one employee demographic information template is configured as at least one presentation panel;
    providing, by the hardware/software architecture executing the one or more programs, at least one application portal to allow at least one authorized user access to the application, wherein the at least one application portal is extendable to one or more additional authorized users by the at least one authorized user to permit the one or more additional authorized users access, by the hardware/software architecture executing the one or more programs, to all or a limited portion of at least one of the presentation panels and the employee benefits management plan data, wherein the at least one authorized user and/or the one or more additional authorized users comprise at least one of an employer, an employee, and a benefit broker/consultant;
    accessing, by a computer system under command of an authorized user, the application such that the authorized user through a plan creator user interface provided by the at least one presentation panel creates a benefit plan using the benefit plan design creation template, wherein at least a plurality of the selectable benefit plan details of the benefit plan design creation template are provided to the authorized user in a dynamic, multi-level format such that selection by the authorized user of one or more of a plurality of options associated with at least one selectable benefit plan detail displayed to the authorized user determines a plurality of selectable benefit plan details and one or more associated valid benefit plan options to be subsequently displayed to the authorized user;
    providing access to the application, by the hardware/software architecture executing the one or more programs, such that at least one additional authorized user through an employee demographic information template interface configured as at least one presentation panel can enter employee demographic information comprising personal health statement information to be used by more than one benefit provider of a plurality of benefit providers, wherein the at least one additional authorized user having access to the employee demographic information template interface comprises an employee, wherein at least a plurality of the selectable details of the at least one employee demographic information template are provided to the additional authorized user in a dynamic, multi-level format such that selection by the additional authorized user of one or more of a plurality of options associated with at least one selectable detail displayed to the additional authorized user determines a plurality of selectable details and one or more associated valid options to be subsequently displayed to the additional authorized user;
    entering, by one or more employees, employee demographic information comprising personal health statement information using the employee demographic information template interface provided to the one or more employees by at least one computer system, wherein entering the employee demographic information by each of the one or more employees comprises using the dynamic, multi-level format to present a plurality of selectable details and one or more associated valid options to the employee upon selection by the employee of one or more of a plurality of options associated with at least one selectable detail such that valid employee demographic information comprising personal health statement information to be used by more than one benefit provider of the plurality of benefit providers is gathered;
    generating, by the hardware/software architecture executing the one or more programs, a benefit plan request for proposal comprising at least one benefit plan and employee demographic information comprising personal health statement information to be used by each of the plurality of benefit providers; and
    receiving from each of the plurality of benefit providers a benefit plan request for proposal response created by at least one computer system using the employee demographic information that comprises the personal health statement information entered by each of one or more employees using the employee demographic information template interface.

2. The method of claim 1, wherein the method further comprises generating, using the application, a benefit plan request for proposal calculated response based on the benefit plan request for proposal.

3. The method of claim 1, wherein the method further comprises generating, at an external benefit provider, a benefit provider request for proposal response based on the benefit plan request for proposal.

4. The method of claim 1, wherein the method further comprises allowing one or more of a benefit/broker consultant, an employer/client, an employee, and a benefit provider to access all or a limited portion of at least one of the presentation panels and the employee benefits management plan data.

5. The method of claim 4, wherein the method further comprises allowing one or more of a benefit/broker consultant, an employer/client, an employee, and a benefit provider to create, delete or modify a benefit plan.

6. The method of claim 4, wherein the method further comprises allowing one or more of a benefit/broker consultant, an employer/client, an employee, and a benefit provider to create, delete or modify employee demographic information.

7. The method of claim 1, wherein the method further comprises allowing an employer/client, after the employer/client has adopted a benefit plan, to perform one or more employee benefit management functions.

8. The method of claim 7, wherein allowing an employer/client to perform one or more employee benefit management functions comprises allowing the employer/client access to change demographic data associated with the benefit plan.

9. The method of claim 1, wherein the method further comprises allowing an employee, after an employer/client has adopted a benefit plan, access to at least a portion of the employee benefits management data.

10. The method of claim 9, wherein allowing an employee access comprises allowing access to at least benefit provider plan information.

11. The method of claim 1, wherein the method further comprises maintaining the benefit plan based on changes in associated employee/dependent demographic plan data.

12. The method of claim 11, wherein the method further comprises providing plan change notification relating to the modification of the benefit plan.

13. The method of claim 1, wherein the method further comprises mining the employee benefits management plan data for use in generating at least one of a plurality of reports.

14. The method of claim 1, wherein the method further comprises personalized image branding one or more presentation panels used to interface with one or more of a benefit broker consultant, an employer/client, an employee, and a benefit plan provider.

15. The method of claim 1, wherein access to the at least one application portal is implemented using at least an internet connection.

16. The method of claim 1, wherein providing the at least one application portal comprises:
providing a benefit broker/consultant portal to allow at least one benefit broker/consultant access to the application;
providing at least one extension of the benefit broker/consultant portal as at least one satellite portal, wherein the at least one satellite portal is separately configurable by the benefit broker/consultant to extend certain rights to one or more employer/clients for access to the application portal; and
providing one or more child portals corresponding to the one or more employer/clients, wherein each child portal is an extension of the access extended to the respective one or more employer/clients and permits each of the one or more employer/clients to further extend access to the application to one or more additional users, wherein the one or more additional users comprise at least one employee of at least one of the one more employer/clients.

17. The method of claim 16, wherein the method further comprises providing security authorization to control access of users to at least one or more portions of the presentation panels and/or employee benefits management plan data.

18. The method of claim 17, wherein providing security authorization to control access of users to at least one of more portions of the presentation panels and/or employee benefits management plan data comprises:
providing view controllable security of the one or more presentation panels such that access to view or edit the presentation panels is restricted; and
providing data security such that user access to view or edit data of one or more presentation panels is restricted.

19. A computer implemented system for use in providing employee benefit management services, the system comprising:
a hardware/software architecture comprising at least one computer system; and
a central application comprising one or more programs executable by the hardware/software architecture to perform one or more employee benefit functions using an associated relational database, wherein the associated relational database stores employee benefits management plan data, wherein the central application is accessible via one or more user portals by a benefit provider and a benefit/broker consultant, wherein the central application allows the benefit/broker consultant via a user interface to provide one or more employer/clients access to all or certain portions of the employee benefits management data, wherein the employee benefits management plan data comprises:
at least one benefit plan derived from at least one benefit plan design creation template, wherein the at least one benefit plan design creation template comprises at least a plurality of selectable benefit plan details quotable by more than one benefit provider of a plurality of benefit providers, and further wherein the application comprises a plurality of presentation panels to provide information to a user, wherein the presentation panels provide at least one of user perceivable graphical elements and user interaction graphical elements, and further wherein the at least one benefit plan design creation template is configured as at least one presentation panel; and
employee demographic information comprising personal health statement information derived from at least one employee demographic information template, wherein the at least one employee demographic information template comprises at least a plurality of selectable details to be used by more than one benefit provider of a plurality of benefit providers, and further wherein the at least one employee demographic information template is configured as at least one presentation panel;

wherein the central application, under control of the hardware/software architecture executing the one or more programs, allows an authorized user through a plan creator user interface provided by the at least one presentation panel to create a benefit plan using the benefit plan design creation template, wherein at least a plurality of the selectable benefit plan details of the benefit plan design creation template are provided to the authorized user in a dynamic, multi-level format such that selection by the authorized user of one or more of a plurality of options associated with at least one selectable benefit plan detail displayed to the authorized user determines a plurality of selectable benefit plan details and one or more associated valid benefit plan options to be subsequently displayed to the authorized user;

wherein the central application, under control of the hardware/software architecture executing the one or more programs, allows at least one additional authorized user through an employee demographic information template interface configured as at least one presentation panel to enter employee demographic information comprising personal health statement information to be used by more than one benefit provider of a plurality of benefit providers, wherein the at least one additional authorized user comprises an employee, wherein at least a plurality of the selectable details of the at least one employee demographic information template are provided to the additional authorized user in a dynamic, multi-level format such that selection by the additional authorized user of one or more of a plurality of options associated with at least one selectable detail displayed to the additional authorized user determines a plurality of selectable details and one or more associated valid options to be subsequently displayed to the additional authorized user;

wherein the central application, under control of the hardware/software architecture executing the one or more programs, generates a benefit plan request for proposal comprising at least one benefit plan and employee demographic information comprising personal health statement information that is useable by each of the benefit providers, the employee demographic information comprising personal health statement information used in the benefit plan request for proposal comprises employee demographic information entered by each of one or more employees using the dynamic, multi-level format to present a plurality of selectable details and one or more associated valid options to the employee upon selection by the employee of one or more of a plurality of options associated with at least one selectable detail such that valid employee demographic information comprising personal health statement information to be used by more than one benefit provider of the plurality of benefit providers is gathered; and further wherein the central application, under control of the hardware/software architecture executing the one or more programs, receives from each of the plurality of benefit providers a benefit plan request for proposal response created using the employee demographic information that comprises the personal health statement information entered by each of one or more employees using the employee demographic information template interface.

20. The system of claim 19, wherein the central application allows an employer/client, via an interface, to provide one or more employees thereof with access to all or certain portions of the employee benefits management data.

21. The system of claim 19, wherein the central application allows the benefit/broker consultant or the employer/client to be a plan creator, wherein the plan creator is allowed through the plan creator user interface to create a benefit plan using the employee benefits management plan data.

22. The system of claim 19, wherein the central application allows one or more of a benefit/broker consultant, an employer/client, an employee, and a benefit provider to create, delete or modify one or more portions of a benefit plan via a user interface.

23. The system of claim 19, wherein the central application allows one or more of a benefit/broker consultant, an employer/client, an employee, and a benefit provider to create, delete or modify one or more portions of employee demographic information via a user interface.

24. The system of claim 19, wherein the central application is further operable to generate a plan request for proposal calculation response.

25. The system of claim 19, wherein the central application allows access to the benefit plan request for proposal by a benefit provider and provides the benefit provider a user interface for use in providing a request for proposal response.

26. The system of claim 19, wherein the central application permits the benefit broker consultant or an employer/client to perform personalized image branding of one or more user interfaces.

27. The system of claim 19, wherein the system further comprises an interface so as to provide access to one or more of the user portals using an interne connection.

28. The system of claim 19, wherein the central application further provides security authorization to control access of at least one of the benefit/broker consultant, an employer/client, and a benefit provider to at least portions of the presentation panels and/or the employee benefits management plan data.

29. The system of claim 19, wherein the central application provides view controllable security of the one or more presentation panels such that access to view or edit the presentation panels is restricted and data security such that user access to view or edit data of one or more presentation panels is restricted.

30. The system of claim 19, wherein the central application supports a benefit broker/consultant portal to allow at least one benefit broker/consultant access to the application, wherein the central application provides support for at least one extension of the benefit broker/consultant portal as at least one satellite portal, wherein the at least one satellite portal is separately configurable by the benefit broker/consultant to extend certain rights to one or more employer/clients for access to the application.

31. The system of claim 30, wherein the central application supports the provision of one or more child portals corresponding to the one or more employer/clients, wherein each child portal is an extension of the access extended to the respective one or more employer/clients and permits each of the one or more employer/clients to further extend access to the application to one or more additional users, wherein the one or more additional users comprise at least one employee of at least one of the one more employer/clients.

* * * * *

UNITED STATES PATENT AND TRADEMARK OFFICE
CERTIFICATE OF CORRECTION

| | |
|---|---|
| PATENT NO. | : 8,234,222 B2 |
| APPLICATION NO. | : 10/327518 |
| DATED | : July 31, 2012 |
| INVENTOR(S) | : Thompson et al. |

It is certified that error appears in the above-identified patent and that said Letters Patent is hereby corrected as shown below:

Column 48
Line 3 of Claim 27
Delete "interne" and insert --internet--

Signed and Sealed this
Eleventh Day of September, 2012

David J. Kappos
*Director of the United States Patent and Trademark Office*